United States Patent
Kreitinger et al.

(10) Patent No.: US 10,337,859 B2
(45) Date of Patent: Jul. 2, 2019

(54) HIGH-SENSITIVITY GAS-MAPPING 3D IMAGER AND METHOD OF OPERATION

(71) Applicant: Bridger Photonics, Inc., Bozeman, MT (US)

(72) Inventors: Aaron Kreitinger, Bozeman, MT (US); Michael Thorpe, Bozeman, MT (US)

(73) Assignee: Bridger Photonics, Inc., Bozeman, MT (US)

(*) Notice: Subject to any disclaimer, the term of this patent is extended or adjusted under 35 U.S.C. 154(b) by 0 days.

(21) Appl. No.: 15/936,247

(22) Filed: Mar. 26, 2018

(65) Prior Publication Data
US 2018/0216932 A1 Aug. 2, 2018

Related U.S. Application Data

(62) Division of application No. 15/285,550, filed on Oct. 5, 2016, now Pat. No. 9,970,756.
(Continued)

(51) Int. Cl.
*G01B 21/20* (2006.01)
*G01M 3/28* (2006.01)
(Continued)

(52) U.S. Cl.
CPC ............ *G01B 21/20* (2013.01); *G01C 15/00* (2013.01); *G01M 3/28* (2013.01); *G01M 3/38* (2013.01);
(Continued)

(58) Field of Classification Search
CPC ........ G01B 21/20; G01B 21/39; G01B 21/53; G01C 15/00; G01M 3/28; G01M 3/38;
(Continued)

(56) References Cited

U.S. PATENT DOCUMENTS

| 4,593,368 A | 6/1986 | Fridge et al. |
| 4,830,486 A | 5/1989 | Goodwin |

(Continued)

FOREIGN PATENT DOCUMENTS

| WO | 2010127151 A2 | 11/2010 |
| WO | 2014088650 A1 | 6/2014 |

OTHER PUBLICATIONS

Amann, et al., "Laser ranging: a critical review of usual techniques for distance measurement," Optical Engineering, vol. 40(1) pp. 10-19 (Jan. 2001).
(Continued)

*Primary Examiner* — Hina F Ayub
(74) *Attorney, Agent, or Firm* — Dorsey & Whitney LLP

(57) ABSTRACT

Measurement apparatuses and methods are disclosed for generating high-precision and -accuracy gas concentration maps that can be overlaid with 3D topographic images by rapidly scanning one or several modulated laser beams with a spatially-encoded transmitter over a scene to build-up imagery. Independent measurements of the topographic target distance and path-integrated gas concentration are combined to yield a map of the path-averaged concentration between the sensor and each point in the image. This type of image is particularly useful for finding localized regions of elevated (or anomalous) gas concentration making it ideal for large-area leak detection and quantification applications including: oil and gas pipeline monitoring, chemical processing facility monitoring, and environmental monitoring.

12 Claims, 14 Drawing Sheets

Related U.S. Application Data

(60) Provisional application No. 62/237,992, filed on Oct. 6, 2015.

(51) Int. Cl.

| | |
|---|---|
| *G01M 3/38* | (2006.01) |
| *G01N 21/53* | (2006.01) |
| *G01P 5/00* | (2006.01) |
| *G06K 9/00* | (2006.01) |
| *G01C 15/00* | (2006.01) |
| *G01N 21/39* | (2006.01) |
| *G01N 21/17* | (2006.01) |

(52) U.S. Cl.
CPC ............. *G01N 21/39* (2013.01); *G01N 21/53* (2013.01); *G01P 5/00* (2013.01); *G06K 9/00201* (2013.01); *G01N 2021/1793* (2013.01); *G01N 2021/1795* (2013.01)

(58) Field of Classification Search
CPC .............. G01P 5/00; G01N 2021/1793; G01N 2021/1795
See application file for complete search history.

(56) References Cited

U.S. PATENT DOCUMENTS

| | | | |
|---|---|---|---|
| 5,367,399 A | 11/1994 | Kramer | |
| 5,371,587 A | 12/1994 | De Groot et al. | |
| 5,534,993 A | 7/1996 | Ball et al. | |
| 5,768,001 A | 6/1998 | Kelley et al. | |
| 5,859,694 A | 1/1999 | Galtier et al. | |
| 6,822,742 B1 | 11/2004 | Kalayeh et al. | |
| 6,864,983 B2 | 3/2005 | Galle et al. | |
| 7,215,413 B2 | 5/2007 | Soreide et al. | |
| 7,292,347 B2 | 11/2007 | Tobiason et al. | |
| 7,511,824 B2 | 3/2009 | Sebastian et al. | |
| 7,742,152 B2 | 6/2010 | Hui et al. | |
| 7,920,272 B2 | 4/2011 | Sebastian et al. | |
| 8,010,300 B1 | 8/2011 | Stearns et al. | |
| 8,121,798 B2 | 2/2012 | Lippert et al. | |
| 8,294,899 B2 | 10/2012 | Wong | |
| 8,582,085 B2 | 11/2013 | Sebastian et al. | |
| 8,730,461 B2 | 5/2014 | Andreussi | |
| 8,781,755 B2 | 7/2014 | Wong | |
| 9,030,670 B2 | 5/2015 | Warden et al. | |
| 9,559,486 B2 | 1/2017 | Roos et al. | |
| 9,759,597 B2 | 9/2017 | Wong | |
| 9,784,560 B2 | 10/2017 | Thorpe et al. | |
| 9,864,060 B2 | 1/2018 | Sebastian et al. | |
| 9,970,756 B2 | 5/2018 | Kreitinger et al. | |
| 2003/0043437 A1 | 3/2003 | Stough et al. | |
| 2004/0105087 A1 | 6/2004 | Gogolla et al. | |
| 2005/0094149 A1* | 5/2005 | Cannon ................. | G01J 3/4338 356/437 |
| 2006/0050270 A1* | 3/2006 | Elman .................. | G01N 21/359 356/326 |
| 2006/0162428 A1 | 7/2006 | Hu et al. | |
| 2008/0018881 A1 | 1/2008 | Hui et al. | |
| 2008/0018901 A1 | 1/2008 | Groot | |
| 2009/0046295 A1 | 2/2009 | Kemp et al. | |
| 2009/0153872 A1 | 6/2009 | Sebastian et al. | |
| 2010/0091278 A1* | 4/2010 | Liu ........................ | G01J 3/4338 356/318 |
| 2011/0164783 A1 | 7/2011 | Hays et al. | |
| 2011/0205523 A1 | 8/2011 | Rezk et al. | |
| 2011/0273699 A1 | 11/2011 | Sebastian et al. | |
| 2011/0292403 A1 | 12/2011 | Jensen et al. | |
| 2012/0106579 A1 | 5/2012 | Roos et al. | |
| 2013/0104661 A1 | 5/2013 | Klotz et al. | |
| 2014/0036252 A1 | 2/2014 | Amzajerdian et al. | |
| 2014/0139818 A1 | 5/2014 | Sebastian et al. | |
| 2014/0204363 A1 | 7/2014 | Slotwinski et al. | |
| 2015/0019160 A1 | 1/2015 | Thurner et al. | |
| 2015/0185313 A1 | 7/2015 | Zhu | |
| 2016/0123718 A1 | 5/2016 | Roos et al. | |
| 2016/0123720 A1 | 5/2016 | Thorpe et al. | |
| 2016/0202225 A1 | 7/2016 | Feng et al. | |
| 2016/0259038 A1 | 9/2016 | Retterath et al. | |
| 2017/0097274 A1 | 4/2017 | Thorpe et al. | |
| 2017/0097302 A1 | 4/2017 | Kreitinger et al. | |
| 2017/0115218 A1 | 4/2017 | Huang et al. | |
| 2017/0343333 A1 | 11/2017 | Thorpe et al. | |
| 2018/0188369 A1 | 7/2018 | Sebastian et al. | |

OTHER PUBLICATIONS

Barber, et al., "Accuracy of Active Chirp Linearization for Broadband Frequency Modulated Continuous Wave Ladar," Applied Optics, vol. 49, No. 2, pp. 213-219 (Jan. 2010).

Barker, "Performance enhancement of intensity-modulated laser rangefinders on natural surfaces", SPIE vol. 5606, pp. 161-168 (Dec. 2004).

Baumann, et al., "Speckle Phase Noise in Coherent Laser Ranging: Fundamental Precision Limitations," Optical Letters, vol. 39, Issue 16, pp. 4776-4779 (Aug. 2014).

Boashash, "Estimating and Interpreting the Instantaneous Frequency of a Signal—Part 2: Algorithms and Applications", Proceedings of the IEEE, vol. 80, No. 4, pp. 540-568 (Apr. 1992).

Bomse, et al., "Frequency modulation and wavelength modulation spectroscopies: comparison of experimental methods using a lead-salt diode laser", Appl. Opt., 31, pp. 718-731 (Feb. 1992).

Choma, et al., "Sensitivity Advantage of Swept Source and Fourier Domain Optical Coherence Tomography," Optical Express, vol. 11, No. 18, 2183 (Sep. 2003).

Ciurylo, "Shapes of pressure- and Doppler-broadened spectral lines in the core and near wings", Physical Review A, vol. 58 No. 2, pp. 1029-1039 (Aug. 1998).

Dharamsi,"A theory of modulation spectroscopy with applications of higher harmonic detection", J. Phys. D: Appl. Phys 29, pp. 540-549 (Jun. 1995;1996) (Retrieved Jan. 16, 2017).

Fehr, et al., Compact Covariance Descriptors in 3D Point Clouds for Object Recognition, 2012 IEEE International Conference on Robotics and Automation, pp. 1793-1798, (May 2012).

Fujima, et al., "High-resolution distance meter using optical intensity modulation at 28 GHz", Meas. Sci. Technol. 9, pp. 1049-1052 (May 1998).

Gilbert, et al., "Hydrogen Cyanide H13C14N Absorption Reference for 1530 nm to 1565 nm Wavelength Calibration—SRM 2519a", NIST Special Publication 260-137 2005 ED, 29 pages, (Aug. 2005).

Iseki, et al., "A Compact Remote Methane Sensor using a Tunable Diode Laser", Meas. Sci. Technol., 11, 594, pp. 217-220 (Jun. 2000).

Jia-Nian, et al., "Etalon effects analysis in tunable diode laser absorption spectroscopy gas concentration detection system based on wavelength modulation spectroscopy", IEEE SOPO, pp. 1-5 (Jul. 2010).

Johnson, et al., "Using Spin-Images for Efficient Object Recognition in Cluttered 3D Scenes", IEEE Transactions on Pattern Analysis and Machine Intelligence, vol. 21, No, 5, 37 pages (Published May 1999).

Karmacharya, et al., "Knowledge guided object detection and indentification in 3D point clouds", SPIE 9528, 952804-952804-13 (Jun. 2015).

Lu, et al., "Differential wavelength-scanning heterodyne interferometer for measuring large step height", Applied Optics, vol. 41, No. 28, Oct. 1, 2002.

Masiyano, et al., "Use of diffuse reflections in tunable diode laser absorption spectroscopy: implications of laser speckle for gas absorption measurements", Appl. Phys. B 90, pp. 279-288 (Feb. 2008).

Ngo, et al., "An isolated line-shape model to go beyond the Voigt profile in spectroscopic databases and radiative transfer codes", Journal of Quantitative Spectroscopy and Radiative Transfer, 129, pp. 89-100 (Nov. 2013).

(56) References Cited

OTHER PUBLICATIONS

Olsovsky, et al,, "Chromatic Confocal Microscopy for Multi-depth Imaging of Epithelial Tissue," Biomedical Optics Express, vol. 4, No. 5, pp. 732-740 (May 2013).

Paffenholz, "Direct geo-referencing of 3D point clouds with 3D positioning sensors", (Doctoral Thesis), Leibniz Universität Hannover, 138 pages (Sep. 2012).

Polyanksy, et al., "High-Accuracy CO2 Line Intensities Determined from Theory and Experiment", Physical Review Letters, 114, 5 pages (Jun. 2015).

Rao, "Information and the accuracy attainable in the estimatin of statistical parameters", Bull. Calcutta Math, Soc., 37,pp. 81-89 (1945, reprinted 1992) (Retrieved Jan. 10, 2017).

Riris, et al., "Airborne measurements of atmospheric methane column abundance using a pulsed integrated-path differential absorption lidar", Applied Optics, vol. 51, No. 34, pp. 8296-8305 (Dec. 2012).

Roos, et al., "Ultrabroadband optical chirp linearization for precision metrology application", Optics Letters, vol. 34 No. 23, pp. 3692-3694 (Dec. 2009).

Rothman, et al., "The HITRAN 2008 molecular spectroscopic database", Journal of Quantitative Spectroscopy & Radiative Transfer, 110, pp. 533-572 (Jul. 2009).

Rusu, et al., "Fast Point Feature Histograms (FPFH) for 3D Registration", IEEE Int. Conf. Robot., pp. 3212-3217 (May 2009).

Sandsten, et al., "Volume flow calculations on gas leaks imaged with infrared gas-correlation", Optics Express, vol. 20, No. 18, pp. 20318-20329 (Aug. 2012).

Sheen, "Frequency Modulation Spectroscopy Modeling for Remote Chemical Detection", PNNL 13324, 51 pages (Sep. 2000).

Silver, "Frequency-modulation spectroscopy for trace species detection: theory and comparison among experimental methods", Appl. Opt., vol. 31 No. 6, pp. 707-717 (Feb. 1992).

Sirat, et al., "Conoscopic Holography," Optics Letters, vol. 10, No. 1 (Jan. 1985).

Stone, et al., "Performance Analysis of Next-Generation LADAR for Manufacturing, Construction, and Mobility," NISTIR 7117 (May 2004).

Twynstra, et al., "Laser-absorption tomography beam arrangement optimization using resolution matrices", Applied Optics, vol. 51, No. 29, pp. 7059-7068 (Oct. 2012).

Xi, et al., "Generic real-time uniorm K-space sampling method for high-speed swept-Source optical cohernece tomography", Optics Express, vol. 18, No. 9, pp. 9511-9517 (Apr. 2010).

Zakrevskyy, et al., "Quantitative calibration- and reference-free wavelength modulation spectroscopy", Infrared Physics & Technology, 55, pp. 183-190 (Mar. 2012).

Zhao, et al., "Calibration-free wavelength-modulation spectroscopy based on a swiftly determined wavelength-modulation frequency response function of a DFB laser", Opt. Exp., vol. 24 No. 2, pp. 1723-1733 (Jan. 2016).

PCT Application No. PCT/US2018/56285 titled "Apparatuses and Methods for a Rotating Optical Reflector" filed on Oct. 17, 2018, pp. all.

\* cited by examiner

HIGH-SENSITIVITY GAS-MAPPING 3D IMAGER AND METHOD OF OPERATION

CROSS REFERENCE TO RELATED APPLICATIONS

This application is a divisional of U.S. patent application Ser. No. 15/285,550, filed Oct. 5, 2016 and issued as U.S. Pat. No. 9,970,756 on May 15, 2018, which claims the benefit of U.S. Provisional Application No. 62/237,992, filed Oct. 6, 2015. The afore-mentioned applications, and issued patent, are incorporated herein, in their entirety, and for any purpose.

STATEMENT REGARDING RESEARCH & DEVELOPMENT

This invention was made with government support under DE-AR0000544 awarded by the Department of Energy. The government has certain rights in the invention.

FIELD OF THE INVENTION

The present invention generally relates to the field of optical sensors for remote gas concentration measurements.

BACKGROUND OF THE INVENTION

Wavelength modulation spectroscopy (WMS) has long been the preferred technique for high-accuracy remote path-integrated gas concentration measurements due to its high-sensitivity and inherent immunity to many sources of measurement noise and bias. (See, e.g., Bomse, D. S., et. al., "Frequency modulation and wavelength modulation spectroscopies: comparison of experimental methods using a lead-salt diode laser," Appl. Opt., 31, 718-731 (1992); and Iseki, T., et. al., "A Compact Remote Methane Sensor using a Tunable Diode Laser," Meas. Sci. Technol., 11, 594 (2000).) Due to these benefits there are now several commercially available hand-held sensors based on WMS for remote methane leak detection (See, e.g., the Remote Methane Leak Detector by Heath Associates. US; and a hand-held sensor by Tokyo Gas Co.).

These sensors perform well in leak detection scenarios involving short standoff distances and in relatively small search areas. However, their relatively long measurement times (0.1 s), lack of spatial registration of individual measurements, and lack of distance information to the backscattering target preclude imagery generation, large area scanning, and quantitative concentration analysis.

WMS sensors also exist for longer-range remote methane sensing from helicopters for pipeline leak monitoring. (See, e.g., the Aerial Laser Methane Assessment (ALMA) System offered by Pergam Technical. Services.) This type of sensor suffers from many of the same limitations as the hand-held devices. Its slow measurement acquisition time (0.04 s) precludes spatial scanning of the WMS beam and results in a data product consisting of a single line of measurements roughly positioned around the pipeline. The line measurement format precludes many desired data products including leak localization, quantitative estimates of total leaked gas and gas flux estimates.

Many emerging gas detection applications will benefit from rapidly-acquired, accurate, quantitative, and long range gas concentration imagery covering large measurement areas. Examples include emissions monitoring of methane, $CO_2$ and other hazardous gases from large industrial facilities to comply with new air pollution standards set forth by the EPA, pipeline leak detection and monitoring, and environmental terrestrial monitoring to understand large-scale sources and sinks of greenhouse gases and how they contribute to climate change.

The disclosed systems and methods herein teach how to create accurate and precise path-integrated gas concentration imagery of a scene from a collection of spatially-scanned and -encoded WMS measurements. It also teaches how the path-integrated gas concentration imagery can be converted into path-averaged gas concentration imagery with the addition of spatially encoded distance measurements to objects in the scene. It is shown that path-averaged gas concentration imagery may be superior to path-integrated gas concentration imagery for applications requiring high-sensitivity detection of regions containing elevated (or otherwise anomalous) gas concentration. Also, methods are presented for rapid measurement processing via a simplified representation of the WMS signal model to permit timely generation of gas concentration imagery with reduced systematic measurement errors.

SUMMARY OF THE INVENTION

A measurement system is provided that is configured to precisely and accurately measure spatially-encoded, gas absorption measurements, comprising: a wavelength modulation spectroscopy portion configured to measure a gas absorption of laser light over a distance to a surface; a spatially-scanning transmitter configured to transmit laser light used for wavelength modulation spectroscopy in a prescribed direction; an encoder configured to measure a direction of transmitted laser light used for the wavelength modulation spectroscopy; and a processor configured to process transmitter encoder and gas absorption measurements, and to assign a direction of transmitted laser light to a gas absorption measurement from the wavelength modulation spectroscopy portion to enable the creation of spatially mapped gas absorption imagery.

A measurement system is provided that is configured to precisely and accurately measure spatially-encoded, gas concentration measurements, comprising: a wavelength modulation spectroscopy portion configured to measure a gas absorption of laser light over a distance to a surface; a laser detection and ranging portion configured to measure a distance from a sensor to the surface; a spatially-scanning transmitter configured to transmit laser light used for laser wavelength modulation spectroscopy and/or laser detection and ranging in a prescribed direction; an encoder configured to measure a direction of transmitted laser light; and a processor configured to assign the direction of transmitted laser light to a gas absorption measurement from the wavelength modulation spectroscopy portion, and to a distance measurement from the laser detection and ranging portion to enable the creation of spatially mapped gas concentration imagery.

The laser detection and ranging portion may have sufficient resolution and accuracy such that the error in the path-averaged gas concentration measurement is not substantially limited by the error in the laser detection and ranging measurement.

The scanning transmitter may be configured to spatially overlap the laser light used for the wavelength modulation spectroscopy portion with the laser light used for the laser detection and ranging portion.

The measurement system may further comprise: a geo-registration portion that uses GPS and inertial measurement unit (IMU) measurements together with a direction measurement from the encoder and the distance measurement to the surface to enable geo-registration of a path-averaged gas concentration measurement to the surface.

A scanning transceiver is provided that is configured to combine laser detection and ranging with laser wavelength modulation spectroscopy (WMS) measurement capabilities, comprising: a laser detection and ranging transmitter portion that transmits a beam for use in measuring a range to a surface; a wavelength modulation spectroscopy transmitter portion that transmits a beam for use in measuring gas absorption between the transceiver and a surface, where the wavelength modulation spectroscopy transmitter is configured to transmit a beam with a larger divergence angle than the laser detection and ranging transmitted beam divergence angle; and a spatial scanning mechanism configured to scan the wavelength modulation spectroscopy and/or laser detection and ranging beams.

The wavelength modulation spectroscopy beam divergence may be configured to substantially match the transceiver telescope field of view.

A sensor is provided that is configured to improve the accuracy in determining gas absorption by compensation of harmonic distortion, comprising: a modulated laser output; a beam splitter configured to split the modulated laser output into a plurality of split output portions; a transmitter configured transmit a first split output portion of the laser light to a surface; a reference module configured to receive a second split output portion, and to produce a reference electrical signal; a receiver configured to receive a scattered portion of the first split output portion from the surface to produce a gas absorption electrical signal; and a processor configured to process the reference signal and the gas absorption signal to generate a gas absorption measurement with reduced errors in accuracy that are due to harmonic distortion on the gas absorption signal.

A method is provided for accurate and real-time determination of gas absorption from a wavelength modulation spectroscopy signal, comprising: modulating an output wavelength of a laser such that the modulation amplitude, modulation frequency, and modulation phase of the laser output are known; transmitting a portion of the laser output to a surface; receiving a portion of the laser output scattered from the surface; producing a laser wavelength modulation spectroscopy signal from the received scattered laser output; preparing an approximate functional form or look up table of the absorption sensitivity coefficient as a function of environmental variables to reduce computation time for a gas concentration measurement; and computing a gas concentration using the laser wavelength modulation spectroscopy signal with the approximate functional form or the look up table of the absorption sensitivity coefficient.

A method is provided for reducing the noise and inaccuracies of wavelength modulation spectroscopy (WMS) gas absorption measurements, comprising: modulating the output of a laser; measuring, or inferring from known behavior of similar lasers, the relative phase between the output amplitude modulation and the output wavelength modulation of the modulated laser output; adjusting the laser bias current, the laser temperature, the input modulation amplitude, or the input modulation frequency, in order to change the relative phase between the output amplitude modulation and the output wavelength modulation of the modulated laser output to be closer to 90 degrees; and using the modulated laser output to perform laser wavelength modulation spectroscopy.

A method is provided for reducing the noise and inaccuracies of wavelength modulation spectroscopy (WMS) gas absorption measurements, comprising: modulating the output of a laser, wherein the laser output modulation is comprised of a plurality of modulation frequencies; and using the modulated laser output to perform laser wavelength modulation spectroscopy whereby the use of the plurality of modulation frequencies reduces the noise on the wavelength modulation spectroscopy signal that is due to speckle interference.

A method is provided for filtering a wavelength modulation spectroscopy (WMS) signal to reduce the noise and inaccuracies of spatially-scanned gas absorption measurements, comprising: modulating an output wavelength of a laser; transmitting a portion of the laser output to a surface; spatially scanning the transmitted portion of the laser output; receiving a portion of the laser output scattered from the surface; producing a laser wavelength modulation spectroscopy signal from the received scattered laser output; and filtering the laser wavelength modulation spectroscopy signal to reduce measurement noise caused by spatially scanning the beam.

Filtering the laser wavelength modulation spectroscopy signal may involve applying an $n^{th}$ order polynomial fit to reduce low-frequency biases from the wavelength modulation spectroscopy signal.

Filtering the laser wavelength modulation spectroscopy signal may involve applying a window function to the wavelength modulation spectroscopy signal.

Filtering the laser wavelength modulation spectroscopy signal may involve applying a window function or $n^{th}$ order polynomial filtering to overlapping portions of the measurement signal such that a measurement duty cycle is substantially greater than 50%.

BRIEF DESCRIPTION OF THE DRAWINGS

The accompanying figures where like reference numerals refer to identical or functionally similar elements and which together with the detailed description below are incorporated in and form part of the specification, serve to further illustrate an exemplary embodiment and to explain various principles and advantages in accordance with the present invention.

DETAILED DESCRIPTION

The current disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Examples are given within this disclosure of embodiments for illustrative purposes only and do not limit applicability of inventive concepts.

1. General Process for WMS Measurements

Techniques for configuring and processing WMS measurements to reduce excess measurement noise caused by spatially-scanning the WMS beam are presented.

Wavelength modulation spectroscopy is a form of laser absorption spectroscopy that utilizes modulation of a laser's wavelength to infer the quantity of a target gas between a transmitter and receiver. The absorption of laser power by the target gas follows the Beer-Lambert law:

$$P_R = P_T e^{-2\int_0^l \alpha(z)dz} = P_T e^{-2\sigma C_{PI}} = P_T e^{-2\sigma C_{ave}l}, \quad (1)$$

where $P_T$ is the transmitted power, $P_R$ is the received power, $\alpha(z)$ is the gas absorption strength as a function of distance along the measurement path, and l is the distance between the transmitter and receiver. (See, the Beer-Lambert Law.) The path-integrated absorption ($\int_0^l \alpha(z)dz$) can be rewritten to express the laser absorption in terms of the molecular absorption cross section $\sigma$, and either the path-integrated gas concentration $C_{PI}$, or path-averaged gas concentration $C_{ave}$ and the path length between the transmitter and receiver l.

Wavelength modulation spectroscopy may often be performed on a target gas species having sharp spectral absorption features such that $\alpha(\lambda)$ is a rapidly varying function of wavelength $\lambda$, and therefore, a small modulation of the laser wavelength may impart a detectable amplitude modulation on the laser beam. A common WMS measurement scenario involves the gas absorption imparting amplitude modulation on the laser beam at twice the modulation frequency, as shown in FIG. 1.

Figure 1:
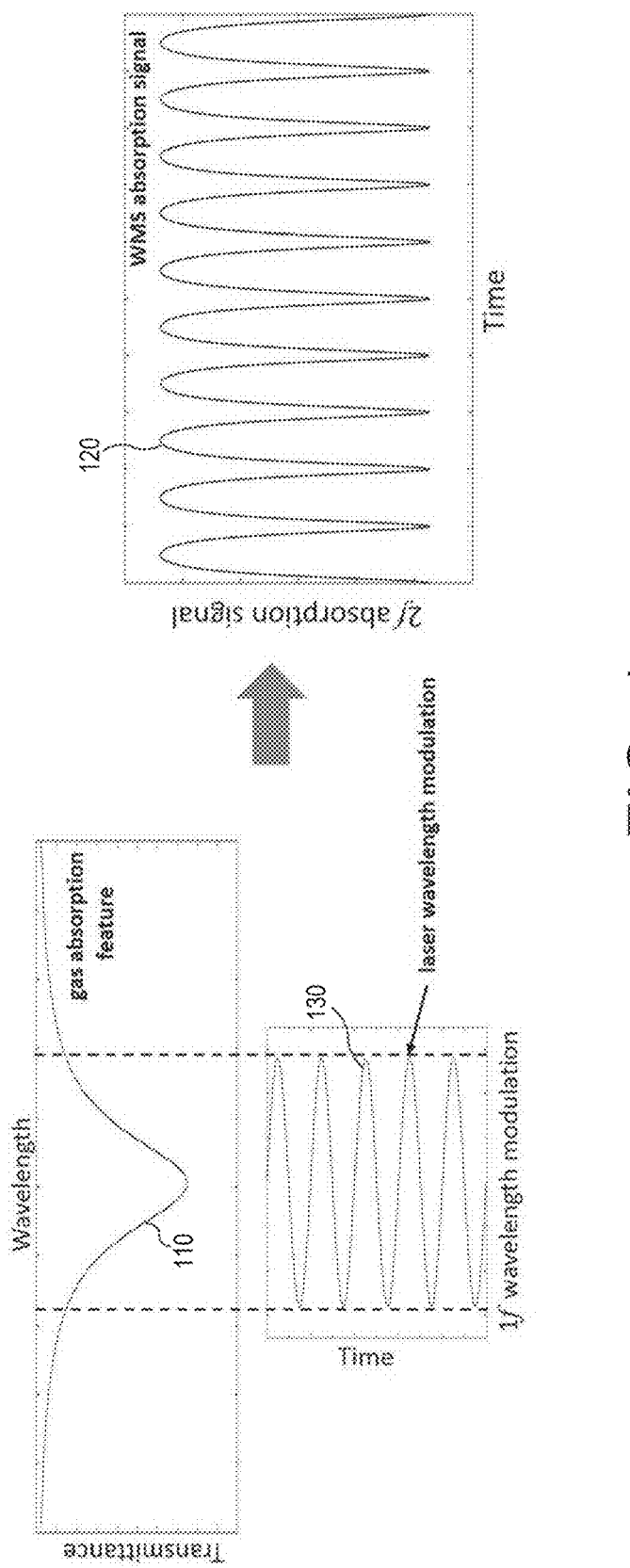
FIG. 1 is a diagram illustrating the wavelength modulation spectroscopy measurement, according to a disclosed embodiment.

As shown in FIG. 1, a gas absorption feature 110 can be converted to a WMS absorption signal 120 using laser wavelength modulation 130.

Many of the measurement bias and noise immunity properties of WMS are derived from the fact that the modulation frequency can be made relatively large (kHz to MHz), and the frequency of the absorption signal is different from the wavelength modulation frequency. (See, Silver, J. A. et. al., "Frequency-modulation spectroscopy for trace species detection: theory and comparison among experimental methods," Appl. Opt., 31, 707-717 (1992)).

When applied to remote sensing, the transmitter and receiver may be collocated, and a portion of the light transmitted to the measurement scene may be scattered to the receiver from either a topographical surface or the molecules in the gas sample. In general, molecular backscattering is extremely weak, often requiring powerful lasers and long integration times to perform single measurements. The present invention addresses topographical backscattering, though the inventive concepts are not limited to topographical backscattering and may be applied to other backscattering. For topographical backscattering, and in the limit of low absorption strength, a simple equation relates the path-integrated gas concentration to the power in the WMS signal at twice the wavelength modulation frequency (2f), $$\frac{P_{2f}}{P_R} = \frac{P_{2f}}{mP_{1f}} = \frac{C_{Pl}}{\gamma} = \frac{C_{ave}l}{\gamma}. \quad (2)$$

Here, $P_{1f}$, $P_{2f}$ and $P_R$ are the signal power at frequencies 1f, 2f and DC; m is the 1f amplitude modulation depth and is a coefficient that relates the gas concentration to the ratio $P_{2f}/P_R$. To reduce noise and systematic errors in WMS measurements, one may impart amplitude modulation on the transmitted WMS laser beam at frequency 1f, and measure the power at frequency 1f on the received light ($P_{1f}$ to infer the amount of received DC power ($P_R$=m·$P_{1f}$) rather than measuring $P_R$ directly. (See, Iseki, T., et. al., "A Compact Remote Methane Sensor using a Tunable Diode Laser," Meas, Sci. Technol., 11, 594 (2000)). This substitution may require precise knowledge of the amplitude modulation depth m. Finally higher-order even harmonics (2nf) where n is an integer, can also be analyzed to provide further improvements to the determination of the gas concentration (See, Dharamsi, A. N., et. al. "A theory of modulation spectroscopy with applications of higher harmonic detection," J. Phys. D., 29, 540 (1996).)

A method for determining the signal strength at harmonics of the modulation frequency for WMS signals is lock-in detection, which is a common practice in the art. Using lock-in detection the signal magnitude ($M_{nf}$) and phase ($\varphi$) of the WMS signal (U) for the $n^{th}$ harmonic of the modulation frequency (nf) are determined as follows:

$$X = \frac{1}{T}\int_{t-T}^{t} \cos(2\pi nft)Udt, \quad (3)$$

$$Y = \frac{1}{T}\int_{t-T}^{t} \sin(2\pi nft)Udt, \quad (4)$$

$$M_{nf} = \sqrt{X^2 + Y^2}, \quad (5)$$

$$\varphi = \tan^{-1}\left(\frac{Y}{X}\right), \quad (6)$$

Here X and Y are the cosine and sine quadrature amplitude measurements, and T is the measurement duration. The gas concentration may be computed from the signal magnitudes according to $$C_{Pl} = \gamma \frac{M_{2f}}{mM_{1f}}.$$

The phase ($\varphi_{nf}$) of the WMS signal at the $n^{th}$ harmonic may be known and phase-sensitive lock-in detection can be used to determine the magnitude according to $$M_{nf} = \frac{1}{T}\int_{t-T}^{t} \sin(2\pi nft + \varphi_{nf})Udt. \quad (7)$$

This approach may yield a more precise estimate of the $n^{th}$ harmonic magnitude because noise in the out-of-phase quadrature is rejected.

The coefficient $\gamma(T,p,\eta,\xi)$ is a function of environmental variables temperature (T) and pressure (p), a set of parameters ($\eta$) that describe the transmitted WMS signal, and a set of parameters ($\xi$) that describe the absorption lineshape. Typically, $\eta$ includes the laser center frequency and the amplitudes, frequencies, and phases of the amplitude modulation (AM) and wavelength modulation (WM) portions of the WMS signal. (See, Zakrevskyy, Y, et. al. "Quantitative calibration- and reference-free wavelength modulation spectroscopy," Infrared Phys, Techn., 55, 183-190 (2012), and Zhao, G. et. at. "Calibration-free wavelength-modulation spectroscopy based on a swiftly determined wavelength-modulation frequency response function of a DFB laser" Opt. Exp., 24, 1723-1733 (2016).)

The set of parameters, $\xi$, includes the gas absorption line intensity, center frequency absorption line and line broadening parameters—including their temperature and pressure dependencies. (See, Rothman, L. S., et. al. "The HITRAN 2008 molecular spectroscopic database" JQSRT, 110 533-572 (2009), and Polyanksy, O. L., et. al. "High-Accuracy $CO_2$ Line Intensities Determined from Theory and Experiment" PRL, 114, 243001 (2015).) Therefore, accurate determinations of the gas concentration require a computation of $\gamma$ via a model of the WMS signal that uses valid measurements of environmental variables as inputs. The computation of can be extended beyond the limit of low absorption to include effects of the Beer-Lambert law by adding an estimate of the absorption strength ($M_{2f}/mM_{1f}$) as another input to the function, $$C_{Pl} = \frac{M_{2f}}{mM_{1f}}\gamma\left(T, p, \frac{M_{2f}}{mM_{1f}}, \eta, \xi\right). \quad (8)$$

In its complete form the calculation of $\gamma$ requires significant computational resources and time that can limit the ability to rapidly process WMS measurements. Specifically, with current reasonably priced commercial computing capabilities, the $\gamma$ computation may become a limiting factor when the WMS measurement rate exceeds approximately 500 Hz, which may be the case when WMS measurements are acquired to generate of gas absorption and gas concentration imagery.

The formalism presented above provides the basic foundation for remote WMS measurements as they may be currently implemented. However, to meet the demands of emerging applications further improvements are required. The following sections of this document outline the current limitations of WMS technology, illustrate why the current limitations may preclude or limit its application to emerging measurement needs, and present solutions to enable the rapid generation of high-sensitivity gas concentration imagery.

The current WMS limitations that may preclude gas concentration imaging can be summarized as follows:

(1) Spatially-mapped, and often geo-registered, path-integrated gas concentration ($C_{PI}$) imagery can be acquired by simultaneously recording large numbers of WMS measurements using a high-power transmitted beam and arrayed detection, or a by using a lower power spatially-scanned and -encoded transmitted beam and a receiver that detects one (or a small number) WMS signals per measurement duration. The present disclosure addresses the latter scanning case, but the inventive concepts disclosed herein are not limited to the scanning case and may be applied to arrayed detection. Current barriers to imaging WMS technology using the scanning case include: slow measurement rates, the lack of beam scanners capable of rapidly scanning the relatively large apertures required for remote WMS measurements, and challenges associated with simultaneous acquisition of the WMS measurements, transmitter encoder measurements, and sensor orientation measurements required to generate path-integrated gas concentration imagery.

(2) High-sensitivity detection of regions with elevated (or otherwise anomalous) gas concentrations may be desired for identification of sources and/or sinks of the target gas. Meeting this need may require measurements of the path-averaged gas concentration ($C_{ave}$) rather than the path-integrated gas concentration ($C_{PI}$), and therefore, concomitant measurements of the distance to the topographical backscatterer.

(3) Rapid generation of gas concentration imagery may require more rapid computations of the γ coefficient to determine the path-integrated gas concentration from measured magnitudes of the WMS signal harmonics.

(4) Rapid and accurate gas concentration imagery may require techniques to mitigate sources of noise and inaccuracy associated with WMS measurements. Noise mitigation may be especially important when the WMS beam is scanned over the measurement scene. Specifically, the variability of the target surface reflectivity and interference effects due to speckle can increase the noise on WMS signals by more than an order of magnitude. These noise sources cause excess broadband noise and harmonic distortion of the WMS signal, and thereby degrade the precision and accuracy of the gas absorption measurements. (See, Masiyano, D., et. al. "Use of diffuse reflections in tunable diode laser absorption spectroscopy: implications of laser speckle for gas absorption measurements." Appl. Phys. B, 90, 279-288 (2008), and Jia-pian, C. et. al., "Etalon Effects Analysis in Tunable Diode Laser Absorption Spectroscopy Gas Concentration Detection System Based on Wavelength Modulation Spectroscopy," IEEE SOPO, pp. 1-5 (2010).) Current technologies rely on long measurement durations to average over sufficient speckle realizations and variations in target reflectivity to reduce the measurement uncertainty, which preclude rapid measurement acquisition and timely generation of gas concentration images.

The following sections of this document present systems and methods for addressing each of the limitations listed above, and describe how these individual solutions can be combined into a device for rapid acquisition and processing of gas concentration imagery. Section 2 presents techniques for acquiring spatially-scanned and -encoded gas concentration and target distance measurements, and explains how this data can be used to create path-averaged gas concentration imagery. An example is provided to motivate the importance of measuring $C_{ave}$ rather than $C_{PI}$. Finally, a transceiver design is presented that enables simultaneous WMS and target range measurements and is compatible with rapidly scanned and encoded measurements. Section 3 covers methods for rapid computation of the γ coefficient to enable timely generation of concentration imagery, and describes methods for reducing WMS systematic measurement errors. Finally, section 4 describes techniques for configuring the laser modulation parameters, and the processing of received signals, to enable rapid and accurate gas concentration measurements by minimizing measurement noise for a wide variety of topographic scenes, backscattering materials, and beam scanning parameters.

2. Spatially-Scanned and -Encoded Gas Concentration and Distance Measurements

This section presents techniques for spatially-scanning, spatially-encoding, and combining remote wavelength modulation spectroscopy (WMS) and target range measurements to enable acquisition of gas concentration imagery. A measurement example is presented to illustrate benefits of combined WMS and target range measurements, guidelines are provided for designing transceivers capable of acquiring high-quality for gas concentration imagery, and example imagery acquired using these techniques is presented.

Figure 2:
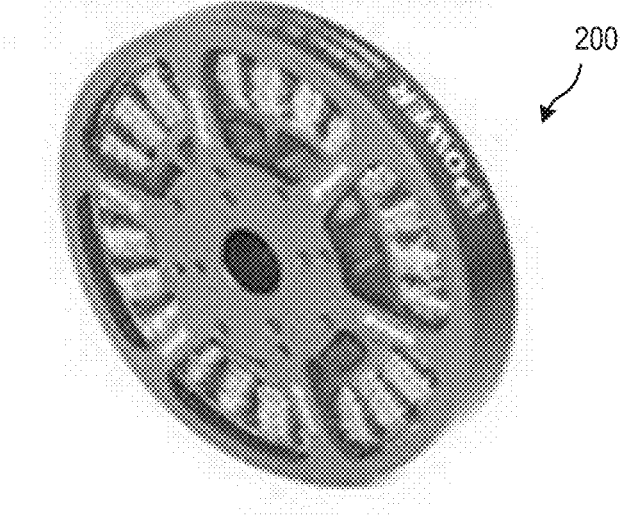
FIG. 2 is drawing of a brushless motor, according to a disclosed embodiment.
Figure 3:
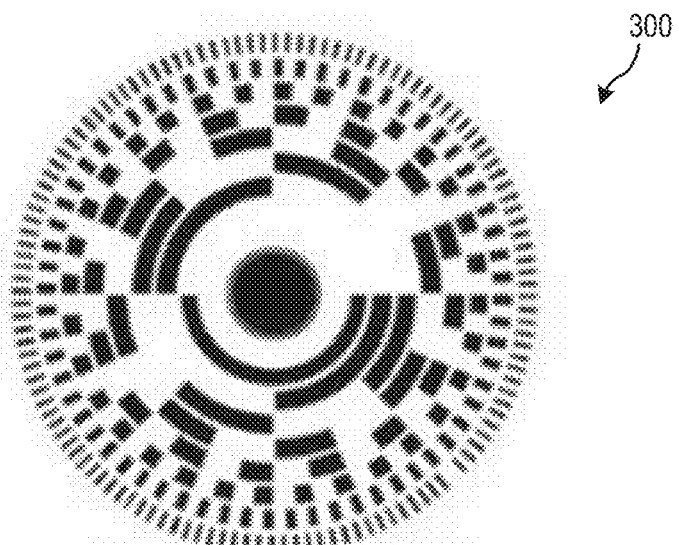
FIG. 3 is a diagram of an angle encoder, according to a disclosed embodiment.

A significant challenge encountered for spatially-scanned WMS measurements, compared with spatially-scanned traditional laser ranging measurements, is the large receive aperture required to collect adequate signals. Smaller receive apertures, which may be easier to scan, may often be used for laser ranging (formally known as laser ranging and detection) due to high peak power of the signals (in the case of pulsed direct detect ranging), or signal amplification provided by a local oscillator (with coherent ranging). Unfortunately, neither of these signal enhancement methods are compatible with rapidly acquired and spatially-scanned WMS measurements. The only options for sensitive detection at longer ranges are increasing the receiver aperture or increasing the transmitted beam power. Further requirements for commercial WMS sensors include eye safe operation and the need for cost-effective laser sources, which limit the degree to which the transmitted laser power can be increased, and which leave increasing the receive aperture area as the only practical design choice. FIGS. 2 and 3 show examples of components and configurations that may be well suited for spatially-scanned and -encoded WMS measurements. Other components and configurations may also be used and are included in this disclosure. FIGS. 2 and 3 show compact brushless motor technology, recently developed for unmanned aerial vehicle (UAV) and gimbal scanner applications that provide large angular accelerations and velocities. These brushless motors (FIG. 2), combined with a high-resolution angle encoders (FIG. 3) can be used to rapidly scan large payloads while accurately measuring the angular orientations of the motor at all times during the scan.

Figure 4:
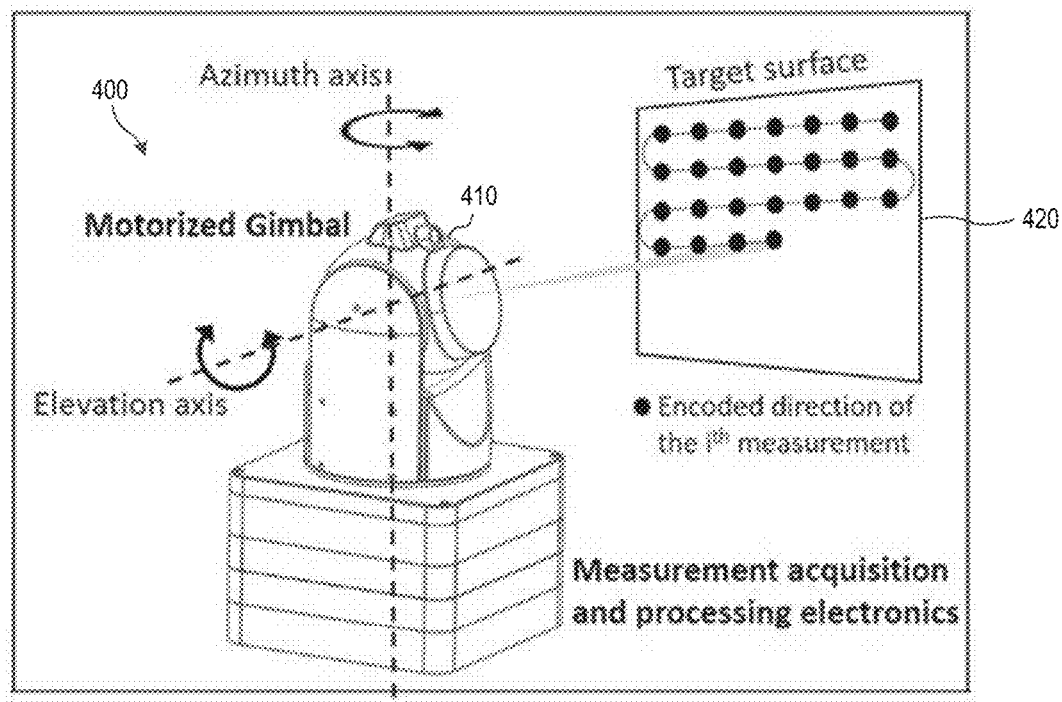
FIG. 4 is a diagram showing a two-axis motorized gimbal configuration for flexible and programmable scan patterns, according to a disclosed embodiment.
Figure 5:
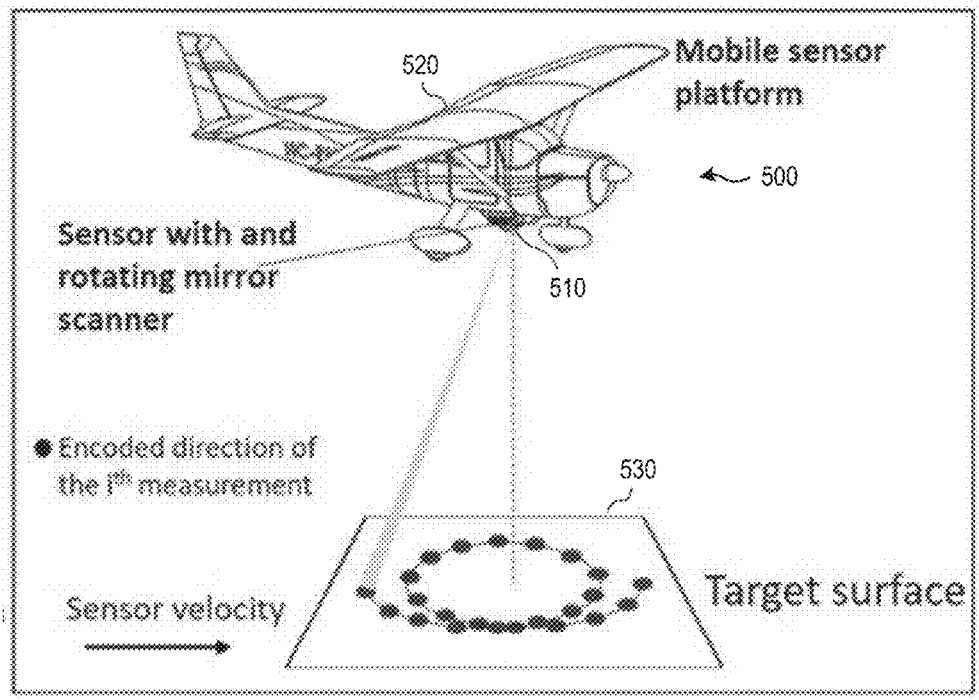
FIG. 5 is a diagram showing a rotating mirror scanner that relies on vehicle motion to push the circular scan pattern over the measurement scene, but allows very rapid beam scanning, according to a disclosed embodiment.

FIGS. 4 and 5 are diagrams showing example systems for generating high-sensitivity gas concentration imagery via spatially-encoded, scanned WMS measurements.

FIG. 4 shows a two-axis motorized gimbal configuration 400 for flexible and programmable scan patterns. As shown in FIG. 4, a motorized gimbal 410, which can be moved along an azimuth axis and an elevation axis, can be used to scan a target surface 420. In this way, a two-axis motorized and encoded gimbal system is provided for programmable WMS beam scanning.

FIG. 5 shows a rotating mirror scanner 500 that relies on vehicle motion to push the circular scan pattern over a measurement scene, and may allow very rapid beam scanning. As shown in FIG. 5, a sensor 510, with a rotating mirror and scanner, is attached to a vehicle 520 (e.g., an airplane), for scanning a target surface 530. Such a vehicle-mounted encoded rotating mirror scanner may be used for mobile WMS measurements.

The gimbal approach may be well suited for smaller receive apertures (typically up to 5" diameter) enabling sensitive gas detection from targets at 0-200 m range. The rotating mirror scanner may be configured for diameters exceeding 10" making it possible to perform WMS measurements from targets approaching 1 km range or more.

For stationary sensor mounting platforms the angle encoder measurements alone may be sufficient to create 2-dimensional images of the path-integrated gas concentration. The addition of range measurements enables generation of 3D topographic imagery and path-averaged gas concentration imagery. Additional measurements of the sensor position and orientation can be used to register this imagery relative to a fixed coordinate system for convenient viewing and/or analysis of multiple datasets, but is not required for the creation of a single image. The situation is more complicated for moving sensor platforms. In this case, continuous knowledge of the sensor position and orientation are required to reconstruct imagery from the point measurement datasets.

A common solution to this problem for traditional laser ranging measurements acquired from a mobile platform is to integrate global positioning system (GPS) and inertial measurement unit (IMU) sensors into the LiDAR scanner. Currently available GPS and IMU sensors can provide sufficient position and orientation uncertainty and rapid update rates. (See, e.g., systems available from Applanix and Vectornav Technologies.) An analogous approach can be taken with the combined range and gas concentration imagery.

When combined with angle encoder, WMS, and range measurements, the sensor position and orientation can be inputted into direct geo-registration algorithms to construct 3D topographic and gas concentration imagery that is registered to a geographic coordinate system (See, Paffenholz, J. A. (2012) "Direct geo-referencing of 3D point clouds with 3D positioning sensors." (Doctoral Thesis), Leibniz Universitat Hannover.)

When a WMS measurements scanned over a scene to create path-integrated gas concentration imagery, it is often impossible to ascertain whether variations in $C_{PI}$ are due to changes in the gas concentration between the sensor and the backscattering target, or if changes in range to the target are responsible for the observed variations. This problem may become the accuracy-limiting factor for gas measurements in topographically complex scenes, for large-area measurements, and measurements of gas species with non-zero background atmospheric concentrations; such as $CO_2$, water vapor, or in large leak situations. A natural solution may be to couple the WMS measurement ($C_{PI}$) with a simultaneous and high-resolution range measurement (R) to allow accurate estimates of the path-averaged gas concentration ($C_{ave}$) between the sensor and the backscattering target, $$C_{ave} = \frac{C_{PI}}{R}. \qquad (9)$$

To illustrate the importance of the range measurement and the determination of $C_{ave}$, an example is provided for atmospheric $CO_2$ measurement. For $CO_2$ the nominal atmospheric concentration is about 400 ppm, and the path-integrated noise for a $CO_2$ imager may be 4 ppm-m in a 1 ms measurement duration. To unambiguously attribute a change in $C_{PI}$ at the 4 ppm-m level to elevated $CO_2$ levels along the measurement path, the distance to the topographical scatterer must be known to better than δR=4 ppm-m/400 ppm=0.01 m. Also, the range measurement should have sufficient resolution to provide certainty that there are not multiple topographical scatterers at ranges that differ by more than 0.01 m along the measurement path, otherwise the determination of $C_{ave}$ may not be accurate.

One possible implementation to measure the backscattering target range R with sufficient resolution, accuracy, and distance window such that the estimate of $C_{ave}$ is not substantially limited by the distance measurement, is via a simultaneous and co-aligned coherent laser ranging and detection (ladar) measurement. Specifically, for this discussion we will consider a type of coherent ladar known as frequency-modulated-continuous-wave (FMCW ladar. (See, Roos, P. A., et. al., "Ultrabroadband optical chirp linearization for precision metrology application" Opt. Lett., 34, 3692 (2009).) FMCW ladar has the benefit that the range measurement resolution is not dependent on the signal digitizer speed, as is the case with traditional time-of-flight ladar. Instead, the resolution (αR) of an FMCW measurement is determined by the bandwidth (B) of the optical frequency sweep that is performed during the measurement duration by $$\Delta R = \frac{c}{2B}. \qquad (10)$$

where c is the speed of light. The FMCW measurement technique is illustrated FIG. 6.

Figure 6:
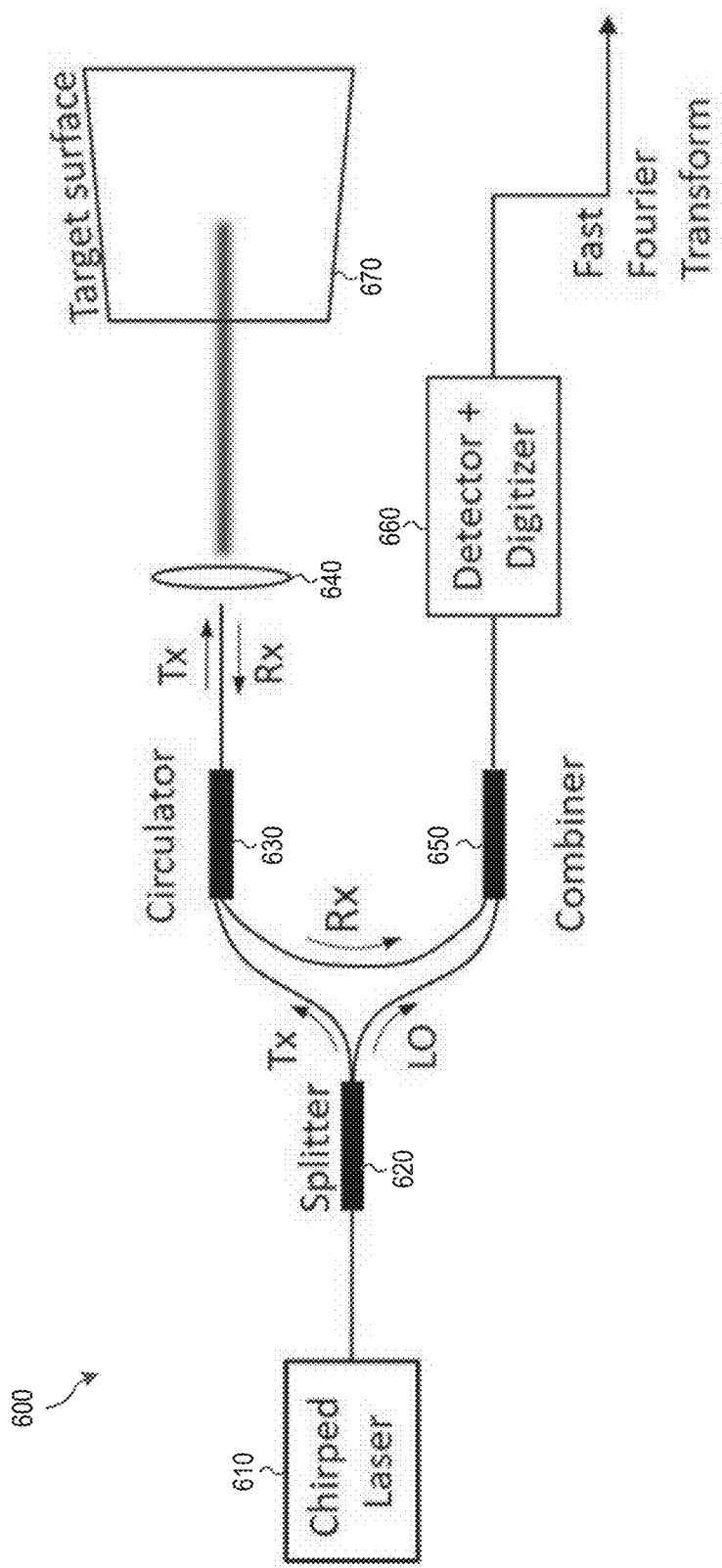
FIG. 6 is a diagram showing a coherent ladar system, according to a disclosed embodiment.

In particular FIG. 6 is an example diagram 600 showing a coherent ladar system 600 that includes a chirped laser 610, a splitter 620, a circulator 630, a lens 640, a combiner 650, and a detector and digitizer 660.

The chirped laser 610 generates a chirped laser beam to be used for distance measuring.

The splitter 620 splits the chirped laser beam into separate beams, one that is provided to the circulator to serve as a transmit beam (Tx) to be transmitted, and one that is provided to the combiner as a local oscillator (LO).

The circulator 630 receives the transmit beam (Tx) and transmits it to a target surface 670 through the lens 640. The circulator 630 also receives a scattered beam (Rx) from the target surface 670, also through the lens 640.

The lens 640 collimates the transmit beam (Tx) for transmission to a target surface 670.

The combiner 650 receives the local oscillator (LO) and the received scattered beam (Rx) and combines the two into a combined beam that is sent to the detector and digitizer 660.

The detector and digitizer 660 converts the optical heterodyne signal created by interfering the local oscillator (LO) and received scattered beam (Rx) into an electrical signal.

Figure 7:
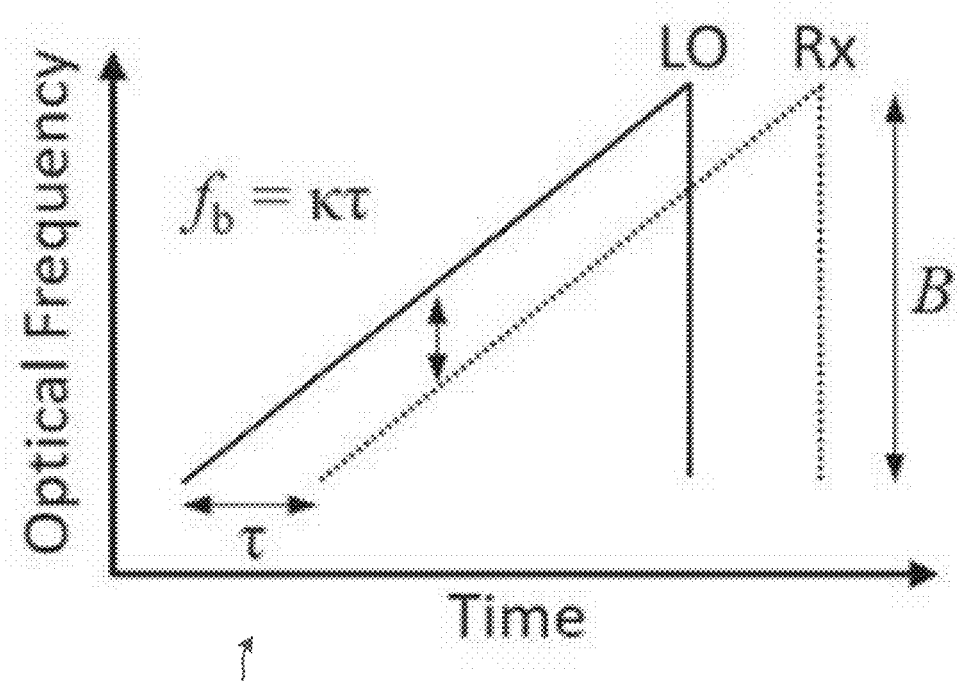
FIG. 7 is a graph of laser frequency vs. time for the received and local copies of the frequency-chirped laser beam in the coherent ladar system of FIG. 6, according to disclosed embodiment.

FIG. 7 is a graph 700 of laser frequency vs. time for the received and local copies of the frequency-chirped laser beam in the coherent ladar system 600 of FIG. 6.

Figure 8:
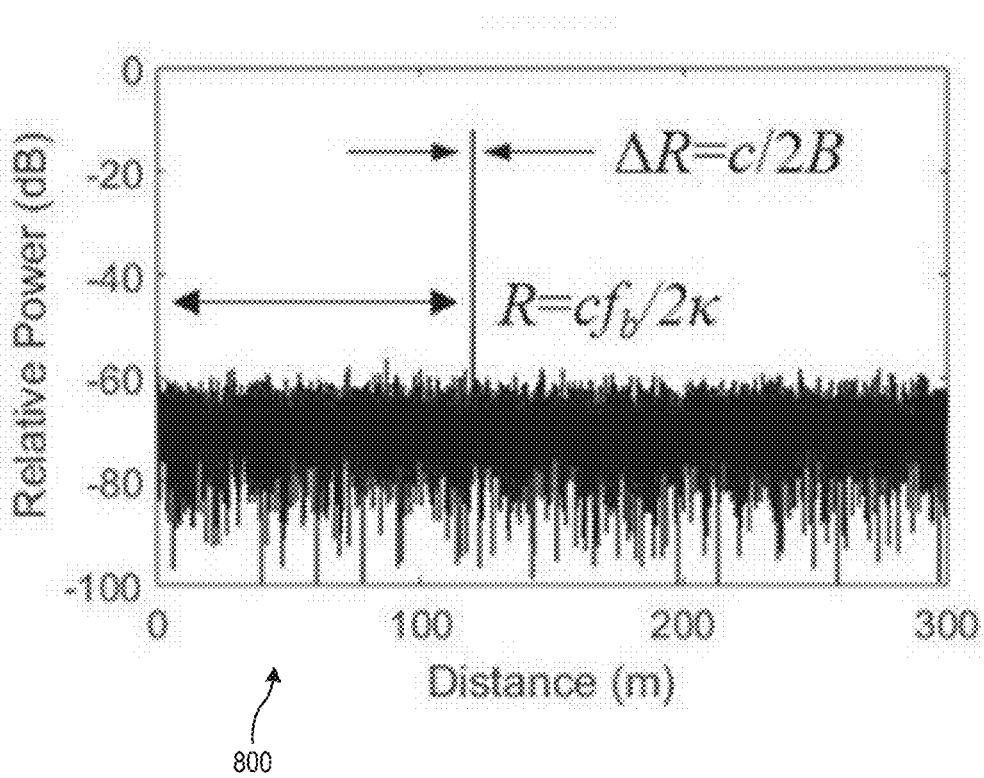
FIG. 8 is a graph of the target range peak after Fourier transforming the digitized ladar signal in the coherent ladar system of FIG. 6, according to a disclosed embodiment.

FIG. 8 is a graph 800 of the target range peak after Fourier transforming the digitized ladar signal in the coherent ladar system 600 of FIG. 6.

Using Equation 10, one may determine that 15 GHz of optical bandwidth is sufficient to achieve 1 cm of resolution on the distance measurement. This bandwidth is easily achieved by commercially available diode lasers, which can readily provide >100 GHz of mode-hop-free optical frequency tuning.

Figure 9:
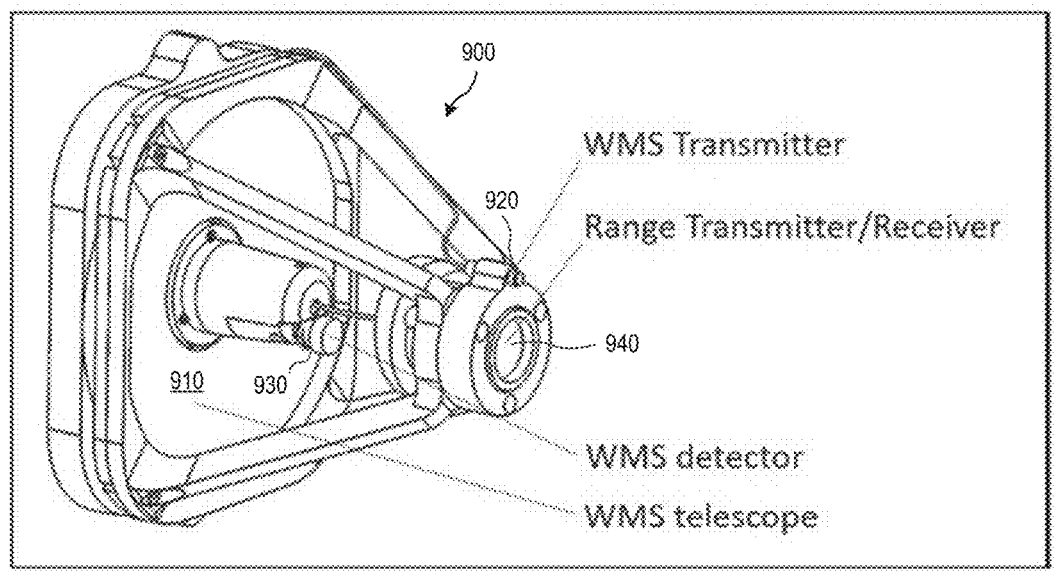
FIG. 9 is a diagram showing a transceiver for spatially-scanned WMS and ranging measurements, according to a disclosed embodiment.
Figure 10:
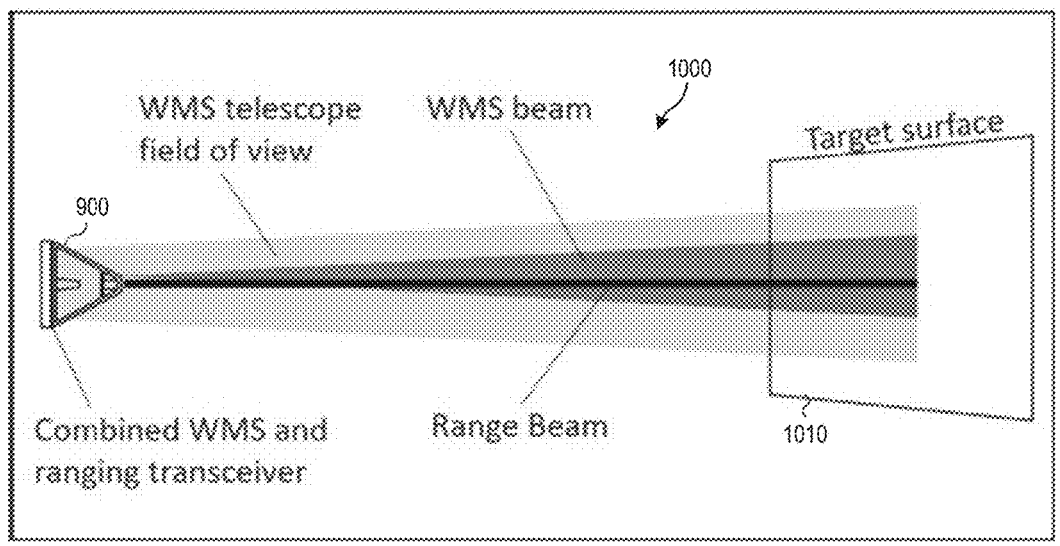
FIG. 10 is a side view of the transceiver of FIG. 9, according to a disclosed embodiment.

Another consideration for performing high-sensitivity remote gas concentration measurements is designing an optical transceiver (optical transmitter and receiver) that may satisfy several different, and often competing, measurement requirements. FIGS. 9 and 10 show a transceiver design exhibiting critical design considerations that enable the simultaneous realization of high-precision and -spatial resolution WMS gas concentration measurements and high-resolution FMCW range measurements, while maintaining the capability for rapid spatial scanning.

FIG. 9 is a diagram showing a transceiver 900 for spatially-scanned WMS and ranging measurements. As shown in FIG. 9, the transceiver 900 includes a WMS telescope 910, a WMS transmitter 920, a WMS detector 930, and a range transmitter/receiver 940.

FIG. 10 is a side view 1000 of the transceiver 900 of FIG. 9, showing its operation with respect to a target surface 1010.

The WMS telescope 910 collects light scattered from target surface 1010 to generate WMS signals. The number of speckle cells imaged by the telescope determines the signal-to-noise-ratio (SNR) of WMS measurements during spatial beam scanning.

The WMS transmitter 920 transmits a diverging WMS beam to a target surface 1010 with beam divergence designed to maximize WMS measurement SNR while meeting desired WMS measurement spatial resolution.

The WMS detector 930 receives a scattered WMS beam from the target surface 1010.

The range transmitter/receiver 940 transmits a FMCW ranging signal to the target surface, and receives a scattered ranging signal.

Optimal ranging may benefit from a transmitted beam that is substantially collimated while optimal WMS measurements may benefit from a transmitted beam divergence that is substantially matched to the WMS telescope field of view. A further desire for optimal WMS measurements may be that the WMS telescope field of view images a sufficient number of speckle cells to produce high-accuracy and low-noise WMS measurements during spatial beam scanning.

Notable features of this example transceiver design include:

(1) Separate transmitters 920, 940 for the WMS and range beams;

(2) An FMCW ranging transmitter with aperture diameter selected to transmit a substantially collimated beam to the target surface;

(3) a WMS transmitter with aperture diameter selected to transmit a diverging beam to the target surface with a divergence angle that substantially matches the WMS telescope field of view; and (4) a compact folded WMS telescope with receive aperture diameter and field of view computed to provide sufficient speckle averaging to meet WMS measurement noise desires while achieving the spatial resolution desires of the WMS measurements. Furthermore, the telescope volume and moment of inertia may be minimized for integration into a motorized two-axis gimbal to enable rapid beam scanning.

The substantially collimated FMCW ranging beam may be designed to transmit a beam with a Rayleigh range of approximately half the distance to the farthest expected target.

A diverging WMS beam is transmitted to reduce the noise caused by speckle interference while maintaining sufficient spatial resolution to create detailed gas concentration imagery. Speckle interference refers to optical interference on the received beam due to macroscopic structure and surface roughness of most target materials, referred to hereafter as diffuse targets, that corrupt WMS gas concentration measurements. Speckle interference may degrade WMS measurements via at least two distinct mechanisms. First, speckle imparts excess signal on the WMS beam at harmonics of the wavelength modulation frequency through wavelength dependent evolution of the speckle pattern. Second, speckle interference leads to excess broadband noise when the beam is scanned over diffuse targets. WMS measurement noise due to speckle interference can be reduced by averaging independent realizations of speckle patterns. (See, Sheen, D. M. "Frequency Modulation Spectroscopy Modeling for Remote Chemical Detection." PNNL, 13324 (2000).) The signal-to-noise ratio (SNR) of WMS measurements from diffuse targets is related to the number of speckle cells ($N_{avg}$) contained in the measurement beam by, $$SNR = \beta A \sqrt{N_{avg}} = \beta A \sqrt{N_{rec} MF_{scan} MF_{v}}, \quad (11)$$

where A is the fractional absorbance and β is the root-mean-squared signal amplitude per unit absorbance, which depends on the absorption shape and the details of the WMS modulation waveform. There are three mechanisms that contribute to the number of speckle cells ($N_{avg}$) averaged in a WMS measurement. The first is the number of speckle cells ($N_{rec}$) imaged by the telescope aperture. The second is a multiplicative factor to account for the number of additional speckle cells ($MF_{scan}$) averaged by spatially scanning the beam. And the third is a multiplicative factor ($MF_v$) to account for the number of additional speckle cells averaged through wavelength modulation of the WMS beam.

The number of speckle cells contained in the measurement beam depends on the beam size on target ($D_{tar}$) and the diameter of the WMS receiver telescope ($D_{rec}$) according to, $$N_{rec} = 1 + \left(\frac{D_{tar} D_{rec}}{\lambda R}\right)^2, \quad (12)$$

where R is the target range and γ is the WMS beam wavelength. The main consequence of Equations 11 and 12, is that a large beam diameter on target and a large receiver aperture with a sufficiently large detector to capture the entire image of beam on target may be desired to reduce WMS measurement noise from diffuse targets. Also, for a given receiver configuration, the WMS measurement noise may be minimized by substantially matching the transmitted beam divergence to the receiver field of view. WMS measurement noise can be further reduced by spatial scanning the measurement beam. The multiplicative factor for the increase in speckle cells included in the measurement due to beam scanning is given by, $$MF_{scan} = 1 + \frac{V T_{meas}}{D_{rec}/2}, \quad (13)$$

where V is the velocity of the beam scanning across the target and $T_{meas}$ is the measurement duration. The consequence of Equation 13 is that faster scanning is desired to reduce speckle noise on WMS measurements. Of course faster scanning is limited by the capabilities of the beam scanner and the spatial resolution requirements of the gas concentration imagery. Finally, the multiplicative factor for the increase in speckle cells averaged due to frequency modulation of the WMS beam may be complicated by dependences on several factors including: the target structure and roughness and the details of the WMS modulation waveform. These dependencies and methods for designing modulation waveforms as well as estimates for the expected noise reduction will be discussed in more detail in section 4.

Figure 11A:
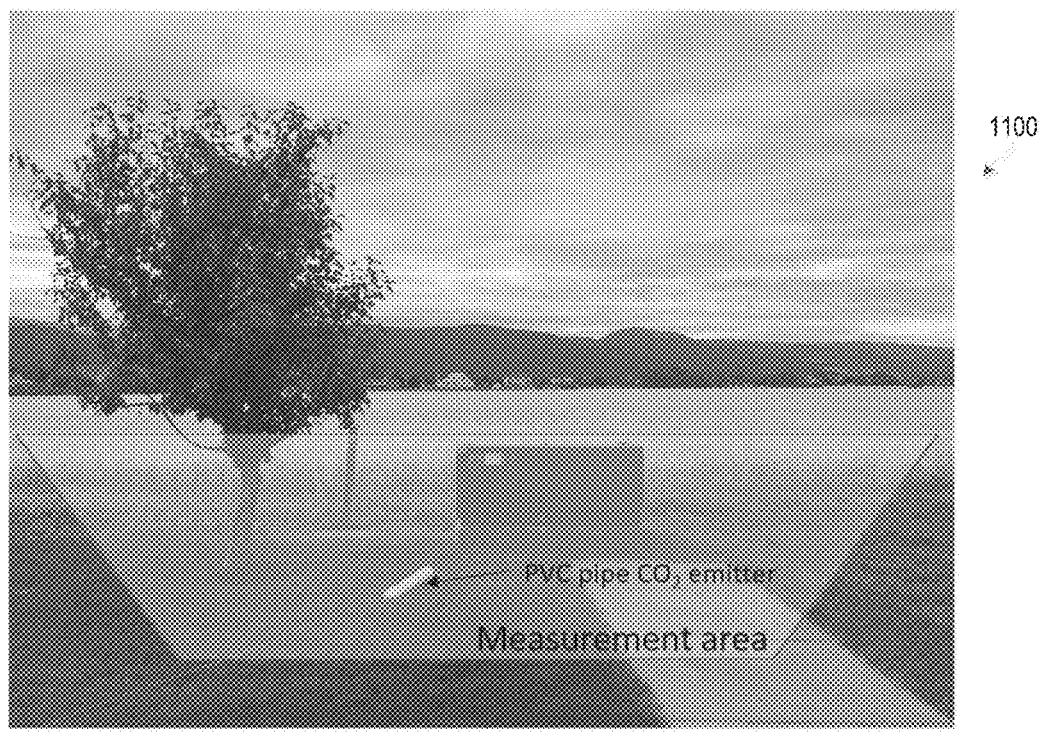
FIG. 11A is a picture of a measurement scene containing a pipe emitting $CO_2$, according to a disclosed embodiment.
Figure 11B:
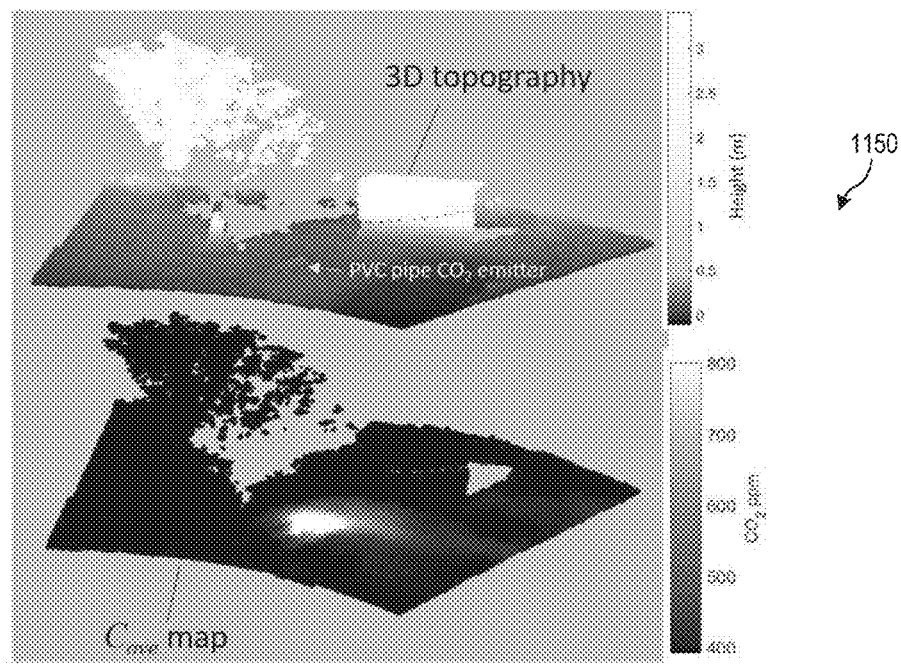
FIG. 11B shows scan data of the measurement scene of FIG. 11A, derived by combining WMS $CO_2$ measurements and FMCW ladar measurements, according to a disclosed embodiment.

The hardware configurations presented in this section enable a combination of high-sensitivity WMS measurements and high-resolution distance measurements which, when combined, result in high-quality gas concentration imagery like the $CO_2$ concentration images shown in FIGS. 11A and 11B.

FIG. 11A is a picture 1100 of a measurement scene containing a pipe emitting $CO_2$. FIG. 11B shows scan data 1150 of the measurement scene of FIG. 11A, consisting of a 3D point cloud (Top) with path-averaged $CO_2$ concentration (Bottom) derived by combining WMS $CO_2$ measurements and FMCW ladar measurements.

Figure 12:
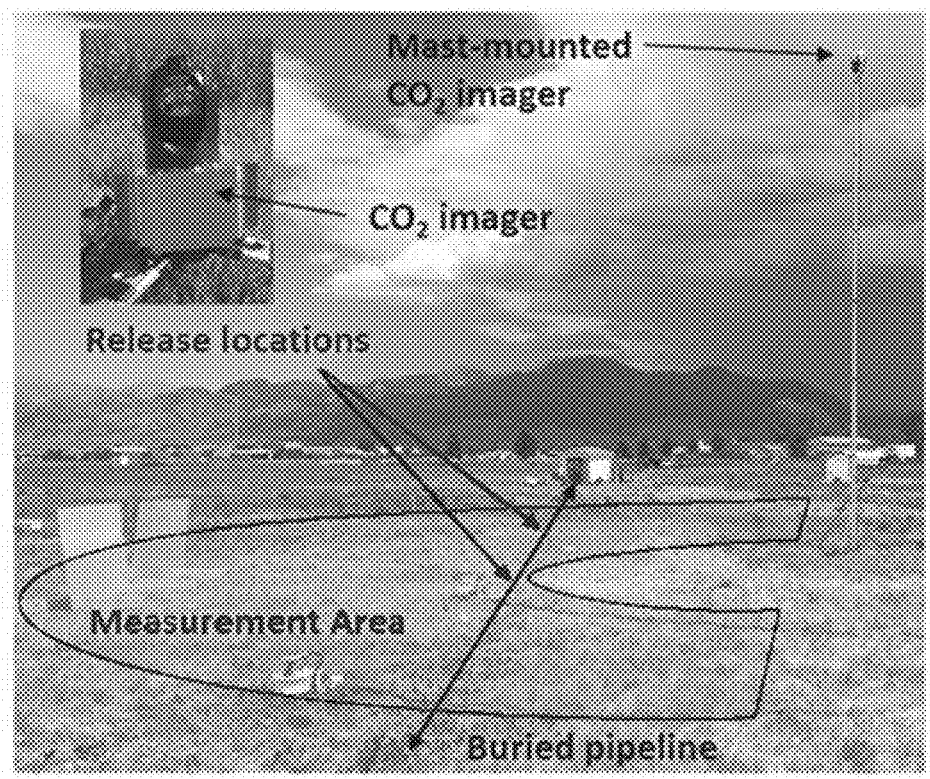
FIG. 12 is a picture of a test site showing the measurement area, sensor, and the buried pipeline, according to a disclosed embodiment.

FIG. 12 is a picture 1200 of a test site showing the measurement area, sensor, and a buried pipeline used for mast-mounted testing of a $CO_2$ gas mapping system.

Figure 13:
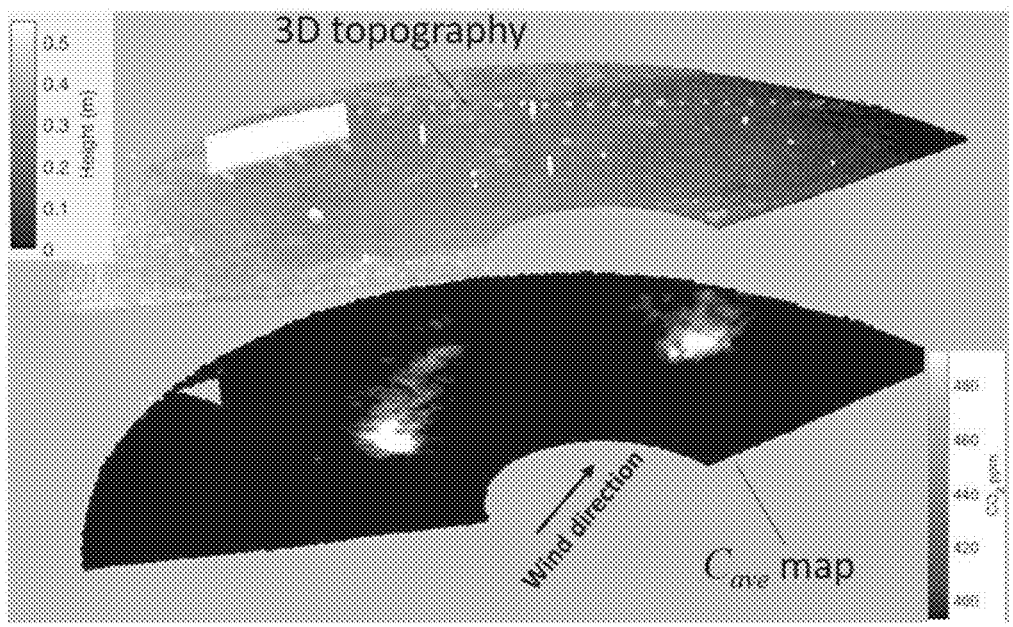
FIG. 13 is a typical scan of the sensor system of FIG. 12, according to a disclosed embodiment.

FIG. 13 is a typical scan 1300 from the sensor system 1200 of FIG. 12, consisting of topographic imagery and $CO_2$ path-averaged gas concentration map clearly indicating the location and extent of the $CO_2$ plumes emanating from the ground.

This capability opens the door to many leak detection approaches that support mobile measurements, measurement automation, and increased measurement efficiency. The next two sections present methods for improving the accuracy WMS measurements and further reducing the noise while the beam is rapidly scanned over the measurement scene.

3. Reduced Sensitivity to Absorption Measurement Noise and Systematic Errors Due to Spatially Scanning the Transmitted Beam In this section we discuss well-known physical models of the WMS measurement found in the literature, and show how this type of model can be used to compute the $\gamma$ coefficient, which relates the measured harmonics of the WMS signal to the path-integrated gas concentration. An analysis of the $\gamma$ coefficient computation time is presented and a discussion of the WMS measurement rate achieved by the present invention will be used to motivate the need for accelerated computations of the $\gamma$ coefficient. Methods are presented for achieving sufficiently rapid $\gamma$ computations for real-time generation of gas concentration imagery based on simplified representations of the WMS model. Finally, descriptions are provided for combining the $\gamma$ computation with shot-to-shot measurements of the transmitted WMS beam to reduce systematic errors in the path-integrated gas concentration measurement.

Many similar formalisms can be found in the literature for high accuracy models of WMS signals. For this discussion we will use the laser model of Zhao, et. al. (See, Zhao, G. et. at. "Calibration-free wavelength-modulation spectroscopy based on a swiftly determined wavelength-modulation frequency response function of a DFB laser" Opt. Exp., 24, 1723-1733 (2016)) and the absorption model of Zakrevskyy (See, Zakrevskyy, Y, et. al. "Quantitative calibration- and reference-free wavelength modulation spectroscopy," Infrared Phys. Techn., 55, 183-190 (2012)). According to Zhao et. al, the time-varying frequency of the laser output for most types of diode lasers can be adequately described by, $$v(t)=v_0+(a_1+b_1 t)\cos(\omega t)+a_2 \cos(2\omega t+\theta_2), \quad (14)$$

where $v_0$ is the laser center frequency, $a_n$ and $b_n$ are the polynomial coefficients for the nth harmonic of the laser's frequency modulation, $\omega$ is the WMS modulation frequency, and $\theta_2$ is the phase shift of the wavelength modulation second harmonic relative to the wavelength modulation first harmonic. Similarly, the laser intensity output for many types of diode lasers can be described by, $$I(t)=I_0(1+i_1 \cos(\omega t+\varphi_1)+i_2 \cos(2\omega t+\varphi_2)), \quad (15)$$

where $I_0$ is the average laser intensity, $i_1$ and $i_2$ are the $1^{st}$ and $2^{nd}$ harmonic intensity modulation amplitudes, and $\varphi_1$ and $\varphi_2$ are the $1^{st}$ and $2^{nd}$ harmonic intensity modulation phases relative to the $1^{st}$ harmonic wavelength modulation. According to Zakrevskyy the time-varying transmission through a gas sample with absorber density N and length l can be described by, $$T(t)=e^{-S\sigma(v(t),T,p,\xi)Nl}, \quad (16)$$

where S is the line intensity and $\sigma$ is the absorption cross-section, which is a function of environmental variables T and p and the absorption lineshape parameters $\xi$. A Voigt lineshape is often used for spectroscopic measurements requiring accuracies no better than a few percent. Higher accuracy spectroscopic measurements have been demonstrated with errors well below one percent through the use of more complicated lineshape models. (See, Ciurylo, R. "Shapes of pressure- and Doppler-broadened spectral lines in the core and near wings." 58, 1029-1039 (1998); and Ngo, N. H., et. al. "An isolated line-shape model to go beyond the Voigt profile in spectroscopic databases and radiative transfer codes." JQRST, 129, 89-100 (2013).) The product of the laser intensity modulation (Equation 15) and the gas sample transmission (Equation 16), is used in the standard lock-in detection integral to calculate the Fourier coefficient magnitudes at harmonics of the wavelength modulation frequency, $$M_f = \frac{1}{T}\int_{t-T}^{t} \sin(2\pi n f t + \varphi_{nf})I(t)T(t)dt. \quad (17)$$

Finally, the relation $$\gamma = C_{PI}\frac{mM_{1f}}{M_{2f}}$$

may be urea to calculate $\gamma$ for specified values of $C_{PI}$, T and p.

Timely generation of high-accuracy WMS concentration imagery may require a method for rapid computation of $\gamma$ from measurements of $$\frac{M_{2f}}{mM_{1f}},$$

T and p, often at rates exceeding 10 kHz. This task can be accomplished by first using the WMS model described above to precompute $\gamma$ with coarse resolution across the range of expected values of $$\frac{M_{2f}}{mM_{1f}},$$

T and p. The model results can then be used to construct a simplified representation of the WMS model that allows rapid computation, typically hundreds to thousands of times faster than the full WMS model, to compute γ for arbitrary values of $$\frac{M_{2f}}{mM_{1f}},$$

T, and p within the precomputed range. Two example methods for creating the simplified representation of the WMS model are a 3-dimensional, $n^{th}$-order polynomial fit of the model results, or the use of interpolation based on a coarse lookup table of the full model results. Below we present an analysis of the measurement accuracy and computational requirements for the multi-dimensional polynomial fit approach.

Computation of γ using the full WMS model for 10 temperatures, 15 pressures, and 25 path-integrated absorptions took 4.1 s (1.1 ms/gamma) using Matlab on a 2.6 GHz Intel i7-5600U processor. Whereas computation of the same gamma values using a 3-dimensional and $5^{th}$ order polynomial fit took 0.02 s (5.3 µs/gamma) using Matlab on the same processor, corresponding to a 200× computation time reduction. Residual errors for polynomial-fitted gamma values compared to the full WMS model calculations reveal a maximum fractional error of 0.06% across all gammas. A subset of the polynomial-fitted gamma values and residuals is shown in FIG. 14.

Figure 14:
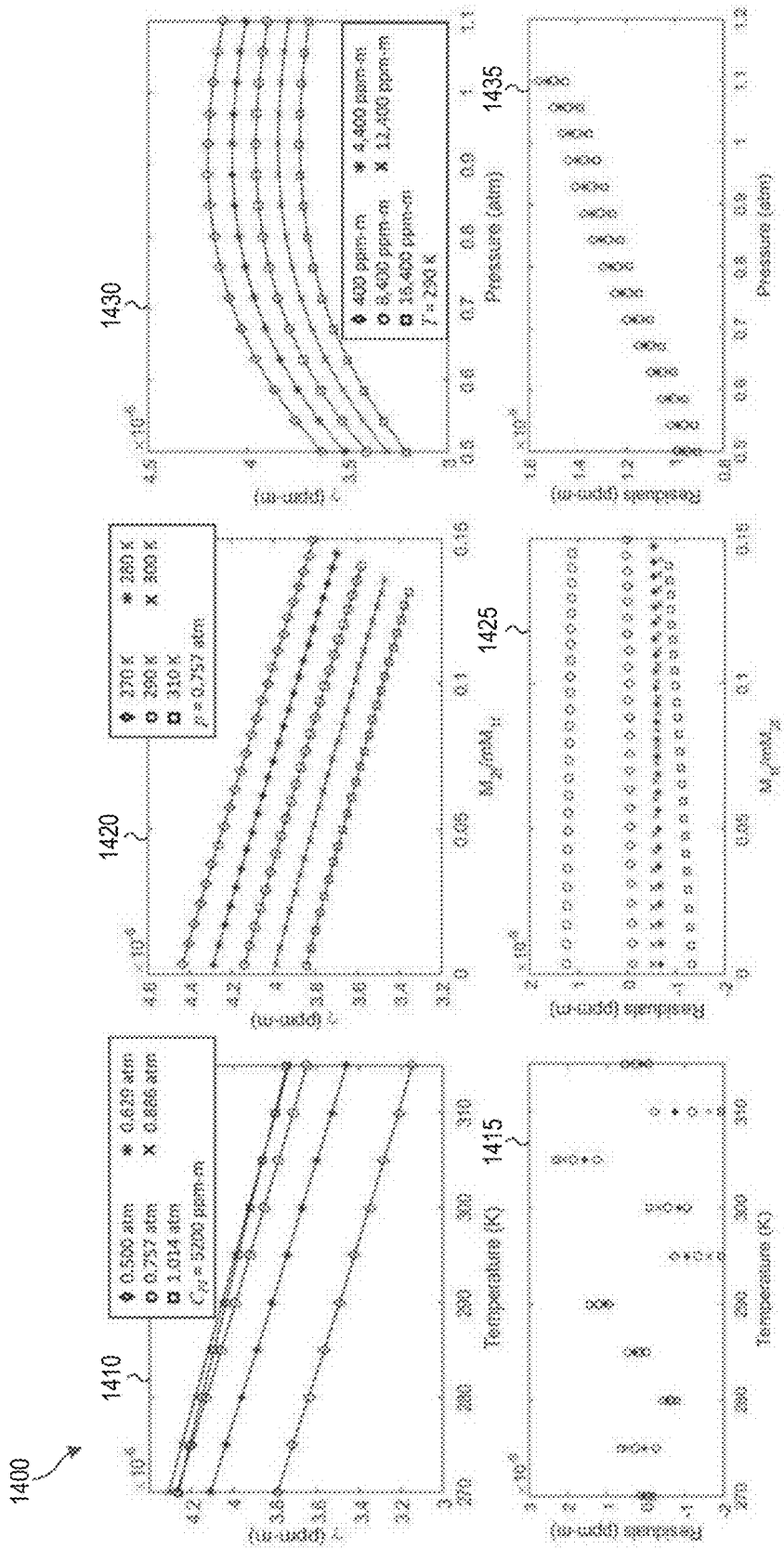
FIG. 14 is a set of graphs of $5^{th}$ order polynomial fit of WMS model results for the 2004 nm $CO_2$ absorption line, according to a disclosed embodiment.

FIG. 14 is a set of graphs 1400 of $5^{th}$ order polynomial fit of WMS model results for a 2004 nm $CO_2$ absorption line, using a modulated laser diode with 4.07 GHz frequency modulation amplitude, 0.28 amplitude modulation depth and −2.71 radians of phase shift between the amplitude modulation (AM) and wave modulation (WM) components. The upper plots show gamma calculated using the WMS model (points) and the polynomial fit (lines) along the temperature 1410, absorption strength 1420, and pressure 1430. The lower plots 1415, 1425, 1435 show residual errors between the WMS model and polynomial fit.

Another benefit of the polynomial fit is the minimal memory requirements as only 56 coefficients must be stored to perform the computation. This is in contrast to the look-up table with interpolation method which would require storage of 10×15×25=3750 gamma values to achieve similar results. In terms of processing speed for creating WMS imagery, the full WMS model may not permit real-time computations of gamma for measurement rates exceeding 1 kpps. This is a serious limitation as many applications require real-time notifications of detected leaks, and measurement rates up to 10 kpps are already being realized. In cases where real-time concentration computations aren't necessary, the accelerated γ computation will likely still be desired. Consider processing a megapixel gas concentration image, the gamma computations alone would take nearly 20 minutes on an average laptop using the full WMS model whereas they would take 5 s using the polynomial fit. Other methods of reducing the γ computation time are also possible.

Next, we will consider systematic errors in WMS measurements. Looking back at Equation 8, it is apparent that accurate WMS measurements may require highly stable values of the amplitude modulation depth m, the ability to distinguish the intended 1f amplitude modulation from other possible sources of 1f signal, and the ability to distinguish 2f portions of the signal that are due to gas absorption from other forms of harmonic distortion that can be present on the WMS beam. A common source of distortion and instability on the transmitted WMS beam is optical amplification. Amplification of WMS beam is often required to increase the range and reduce the duration of WMS measurements. Unfortunately, the amplification process typically causes harmonic distortion of the WMS beam resulting in changes to the value m and the 1f and 2f magnitudes and phases of the transmitted beam. It is also usually the case that the amplifier is less stable than the laser diode used to create the WMS beam, and therefore, the values of m and the 1f and 2f magnitudes and phases on the transmitted beam can vary with time.

To compensate for these effects and to ensure that the received WMS signals result in accurate path-integrated gas concentration measurements, a beamsplitter and photo-detector a used to sample a portion of the WMS beam prior to transmission. The detected signal can then be analyzed to determine the average and shot-to-shot values of m, and the 1f and 2f signal magnitudes and phases on the transmitted beam for a given level of optical amplification. The average values can be incorporated into the intensity modulation term (Equation 15) of the WMS model to improve the accuracy of the gamma computation and the resulting path-integrated gas concentration measurements. The average values of m and the 1f and 2f magnitudes and their shot-to-shot variations can be input into the following equation to further improve the path-integrated gas concentration measurements, $$C_{PI} = \frac{\gamma\left(T, p, \frac{M_{2fR}}{mM_{1fR}}, \eta, \xi\right)}{m}\left(\frac{M_{2fR}}{M_{1fR}} - \left(\frac{M_{2fT}}{M_{1fT}} - \frac{\langle M_{2fT}\rangle}{\langle M_{2fT}\rangle}\right)\right), \quad (18)$$

where $M_{nfT}$ and $M_{nfR}$ are the $n^{th}$ harmonic magnitude for the transmitted and received beams and $\langle M_{nfT}\rangle$ are the average $n^{th}$ harmonic values of the transmitted beam.

4. Reduced Sensitivity to Absorption Measurement Noise and Systematic Errors Due to Spatially Scanning the Transmitted Beam As mentioned in previous sections, during beam scanning the effects of spatial variations in the target reflectivity and speckle interference result in increased noise on WMS measurements. In this section we present methods for configuring the WMS measurement and processing the received signals that reduce the noise for spatially-scanned WMS measurements.

Scanning a WMS beam over a scene of diffuse targets, especially topographically complex targets, dramatically increases the noise compared to stationary measurements. If the WMS measurement system is free of internal etalons, electronic pick-up, and other typical noise sources, the observed excess noise may come from a mixture of speckle interference and variations in target reflectivity that impart amplitude modulation and lead to an increase in the broadband noise floor of the WMS signal. One step toward reducing the excess measurement noise is to remove low frequency fluctuations of the received signal by windowing or filtering, as shown in FIGS. 15-18.

Figure 15:
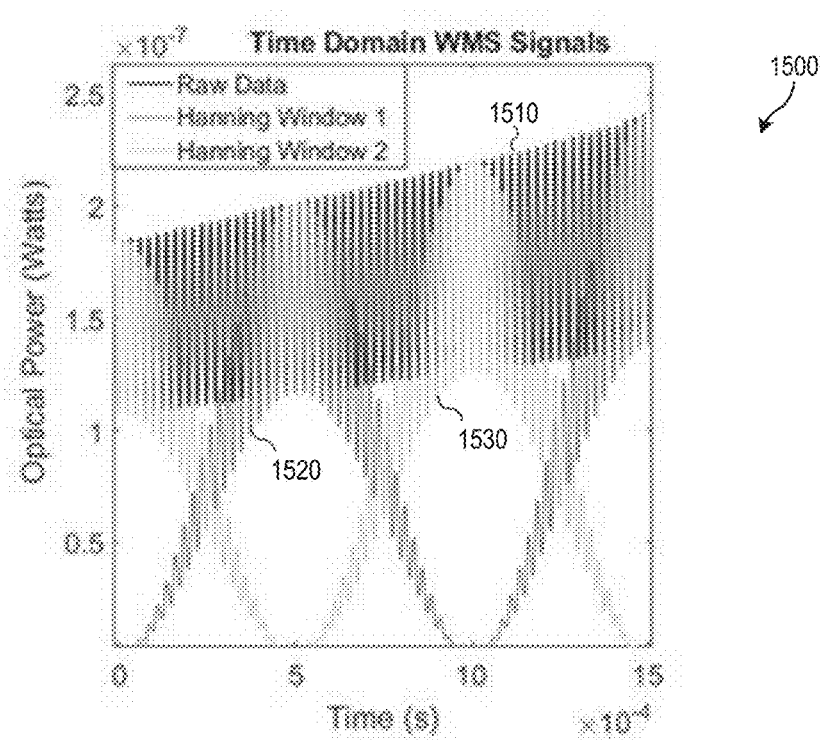
FIG. 15 is a graph of a time domain WMS signal in which overlapping Hanning windows are applied to the received signal to reduce measurement noise without sacrificing measurement duty cycle, according to a disclosed embodiment.
Figure 16:
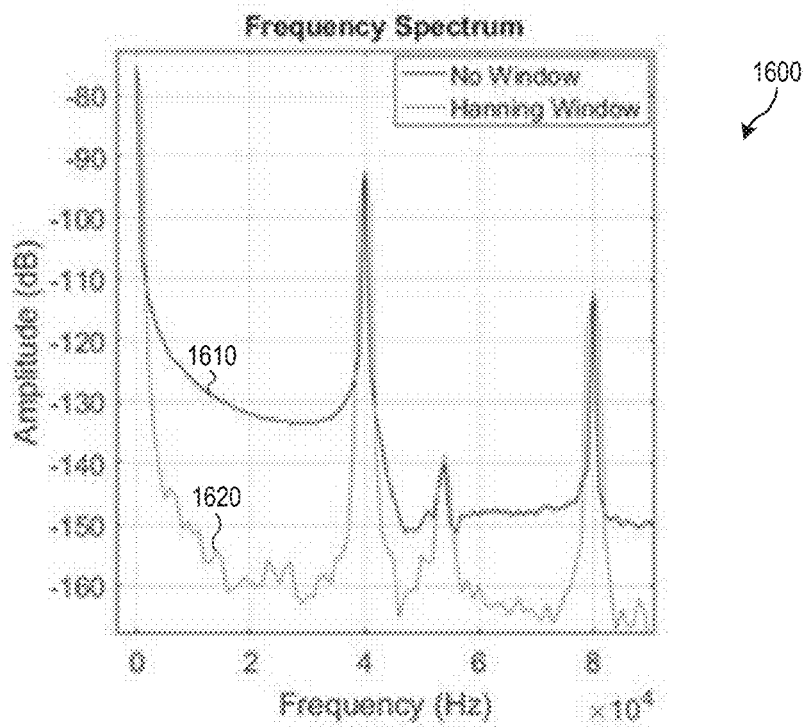
FIG. 16 is a graph of a frequency domain WMS signal showing the observed increase in broadband noise floor when the measurement beam is spatially-scanned and the noise floor reduction achieved with windowing, according to a disclosed embodiment.

FIGS. 15 and 16 show an application of window functions to spatially-scanned WMS measurements. FIG. 15 is a graph 1500 of a time-domain WMS signal in which overlapping Hanning windows are applied to the received signal to reduce measurement noise without sacrificing measurement duty cycle. FIG. 16 is a graph of a frequency domain WMS signal showing the observed increase in broadband noise floor when the measurement beam is spatially-scanned and the noise floor reduction achieved with windowing.

In FIG. 15, Hanning windows 1520, 1530 are applied to the received time-domain WMS signal 1510 to reduce the measurement noise. The windows are overlapped in time with the subsequent window beginning at the peak of the previous window to achieve noise reduction without sacrificing the measurement duty cycle. The resulting power spectra for unwindowed 1610 and windowed 1620 WMS signals, FIG. 16, shows that application of the Hanning window reduces the noise floor by 25 dB for the 1f signal and nearly 20 dB for the 2f signal.

Figure 17:
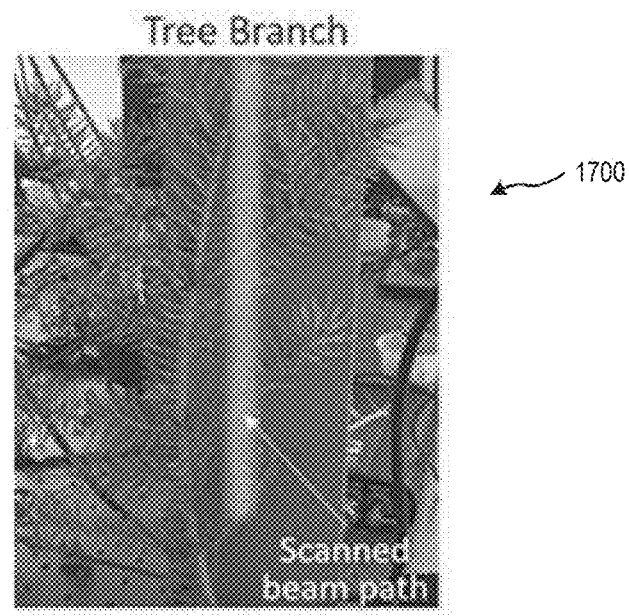
FIG. 17 is an image of a pine branch that was scanned to demonstrate the benefits of filtering for amplitude modulation caused by time-varying reflectivity of complex targets, according to a disclosed embodiment.
Figure 18:
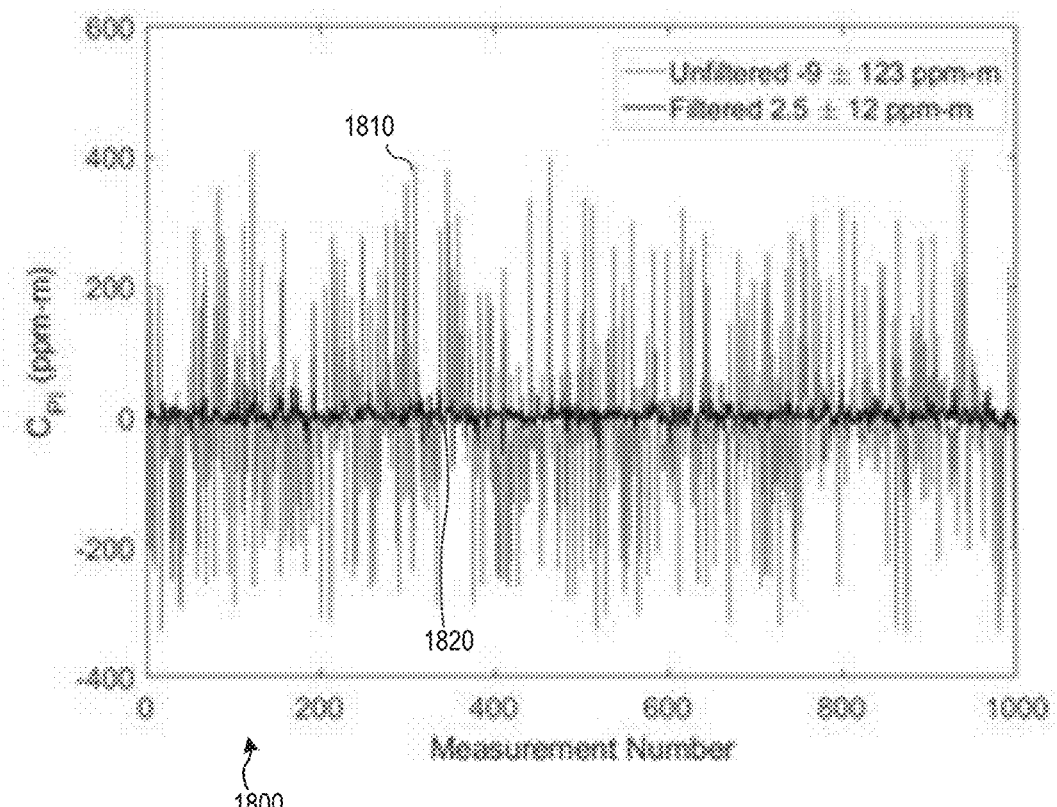
FIG. 18 is a graph showing successive path-integrated absorption measurements with and without filtering, which demonstrates a 10× suppression of scanning noise when filtering is implemented, according to a disclosed embodiment.

Similarly, FIGS. 17 and 18 show noise reductions achieved by implementing a $15^{th}$ order polynomial fit to the time-domain signal to filter off the low frequency baseline in the WMS signal. Specifically, FIG. 17 is an image 1700 of a tree branch with a scanned beam path, and FIG. 18 is a graph 1800 showing an unfiltered signal 1810 and a filtered signal 1820. In this example, application of the polynomial baseline removal reduces the excess noise by a factor of 10. Implementing either the overlapping Hanning window or the polynomial baseline filter leads to similar reductions in measurement noise. Due to its computational simplicity the application of overlapping Hanning windows is the preferred embodiment for the present embodiment.

As shown in FIG. 18, a pine branch was scanned to demonstrate the benefits of filtering low-frequency amplitude modulation caused by time-varying reflectivity of complex targets. As shown in FIG. 17, the measurement scan path of the short-wave infrared WMS measurement beam is shown in transparent white for easy visualization. Successive path-integrated absorption measurements with and without filtering demonstrate a 10× suppression of scanning noise when filtering is implemented. Window functions other than Hanning or other types of filtering, such as low-pass, high-pass, and band-pass may also be used to reduce the noise.

Some residual low frequency noise may still present on spatially-scanned WMS signals after windowing or filtering. An example is shown in FIG. 19.

Figure 19:
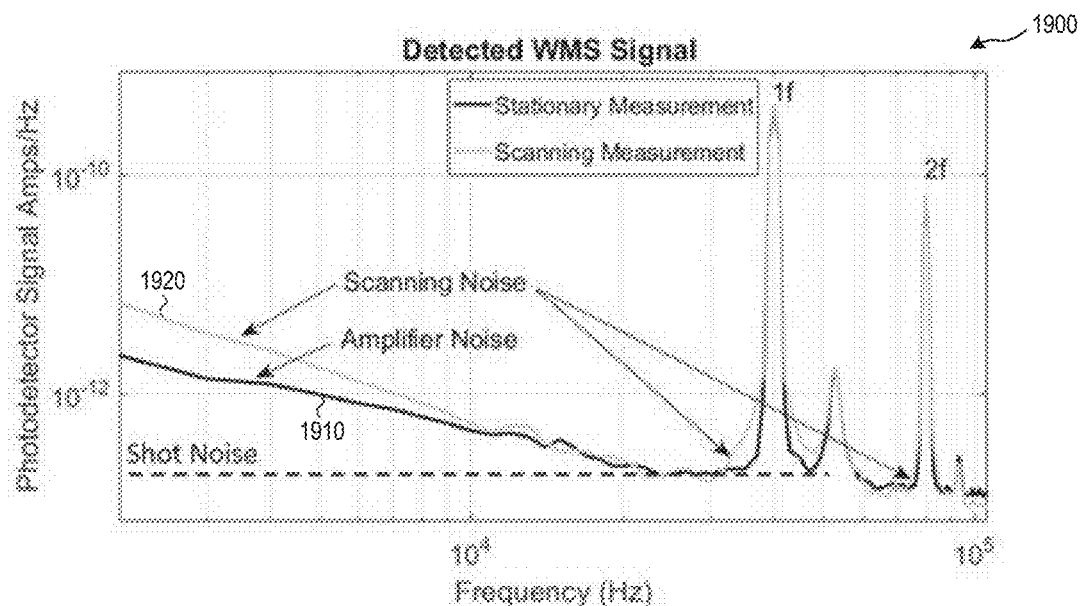
FIG. 19 is a graph of a Fourier-transformed WMS signal for stationary measurement beam and a spatially-scanned measurement beam with a modulation frequency of 40 kHz, according to a disclosed embodiment.

FIG. 19 is a graph 1900 of a Fourier-transformed WMS signal for a stationary measurement beam 1910 and a scanning measurement beam 1920 with a modulation frequency of 40 kHz. The noise floor is shot-noise-limited for frequencies above approximately 20 kHz for both stationary and scanning measurements. In this case a WMS frequency>20 kHz is required to minimize measurement noise.

For this signal, the application of a Hanning window has resulted in a shot-noise-limited noise floor for frequencies above 20 kHz. Below 20 kHz the noise floor is limited by residual scanning noise when the beam is spatially scanned and noise from the optical amplifier when the beam is stationary. Additionally, pedestals of the residual low frequency noise are present at the base of the 1f and 2f harmonics. Additional suppression of residual noise on spatially-scanned WMS measurements can be achieved by configuring the WMS modulation parameters.

For the measurement case shown in FIG. 19, it would be necessary to configure the WMS measurement for a modulation frequency greater than 8 kHz to ensure the WMS measurement signal-to-noise ratio isn't limited by the low frequency noise. A modulation frequency of 40 kHz is used for the preferred embodiment of the present invention to enable rapid WMS measurements (up to $10^4$ measurements per second) while still spectrally resolving the residual low frequency noise and the 1f signal. The modulation frequency is the most straightforward WMS parameter to configure for suppression of scanning noise. Additional noise suppression achieved through careful design of the WMS modulation parameters is discussed in the following paragraphs.

Another modulation parameter that can be configured to reduce noise on spatially-scanned WMS measurements is the phase shift between the amplitude modulation (AM) and wavelength modulation (WM) portions of the signal. In particular, configuring the AM and WM portions to have a relative phase shift of substantially close to $\pi/2$ leads to significant improvements in SNR of gas concentration measurements for targets with low surface roughness, as shown in FIG. 20.

Figure 20:
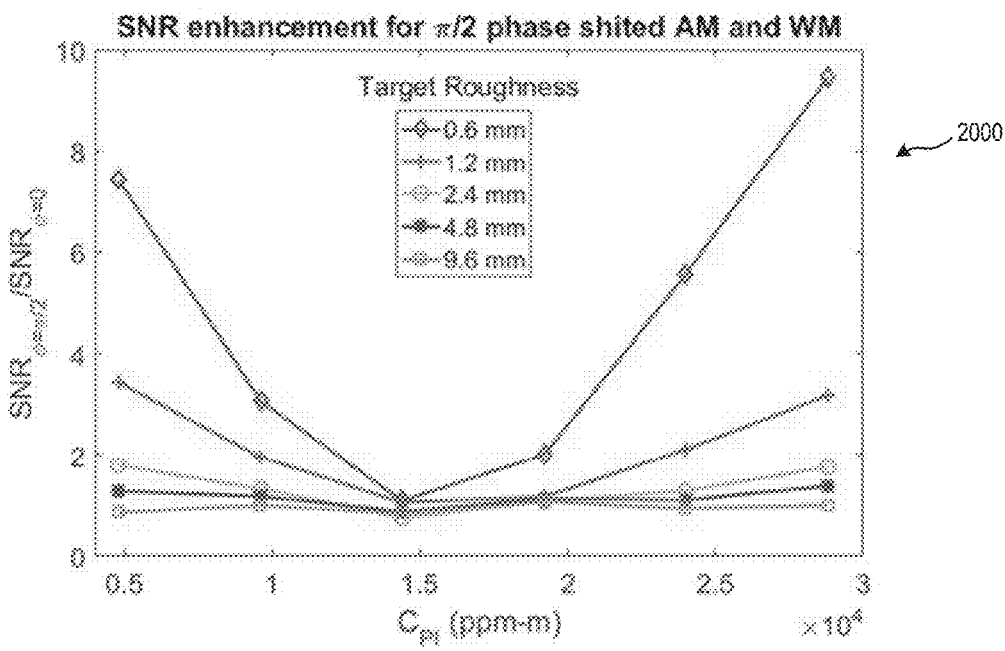
FIG. 20 is a graph 2000 showing results from computer simulations of the ratio of signal to noise ratios for spatially-scanned WMS measurements of $CO_2$ for $\pi/2$ and 0 radian phase shifts between AM and WM modulations versus integrated-path gas concentration ($C_{PI}$) from diffuse targets with different levels of surface roughness, according to a disclosed embodiment.

FIG. 20 is a graph 2000 showing results from computer simulations of spatially-scanned WMS measurements of $CO_2$ versus integrated-path gas concentration ($C_{PI}$) from diffuse targets for different levels of surface roughness. The plot shows the ratio of measurement SNR for a $\pi/2$ radian phase shift between AM and WM modulation divided by the measurement SNR for a 0 radian shift between AM and WM modulations. The WMS measurement configured with a $\pi/2$ phase shift between AM and WM portions shows significantly better performance for diffuse targets with low surface roughness. Improved SNR may be realized for WMS measurements with a $\pi/2$ phase shift between AM and WM portions because the speckle noise imparted on the WMS signal at harmonics of the modulation frequency is in the quadrature with the wavelength modulation (WM) portion and out of quadrature with the amplitude modulation (AM) portion.

According to Equations 2 and 7, the estimate for the received power ($mP_{1f}$) is computed with the amplitude modulation (AM) quadrature of the WMS signal. By implementing a $\pi/2$ phase shift between the AM and WM modulations the speckle interference noise due to spatially-scanning the WMS beam does not contaminate the quadrature of the 1f signal used to compute the denominator of Equation 2. The 2f component of the WMS signal does not benefit from the $\pi/2$ phase configuration because the gas absorption signal and speckle noise both appear in WM quadrature. The SNR enhancement for the $\pi/2$ phase shift configuration is reduced for integrated-path gas concentrations between 10,000 ppm-m and 24,000 ppm-m because the SNR of the 0 radian configuration improves for these gas absorption levels. This happens because the speckle noise on the 1f and 2f harmonics is common mode for low surface roughness targets. Furthermore, in this region the absorption due to the nominal atmospheric $CO_2$ concentration may balance the magnitudes of the common-mode noise on the 1f and 2f signals which may lead to cancellation of the speckle noise in the numerator and denominator in Equation 2. An embodiment of this invention uses $\pi/2$ phase shift between AM and WM modulations so the improved gas concentration SNR can be realized independent of the gas absorption strength.

Figure 21:
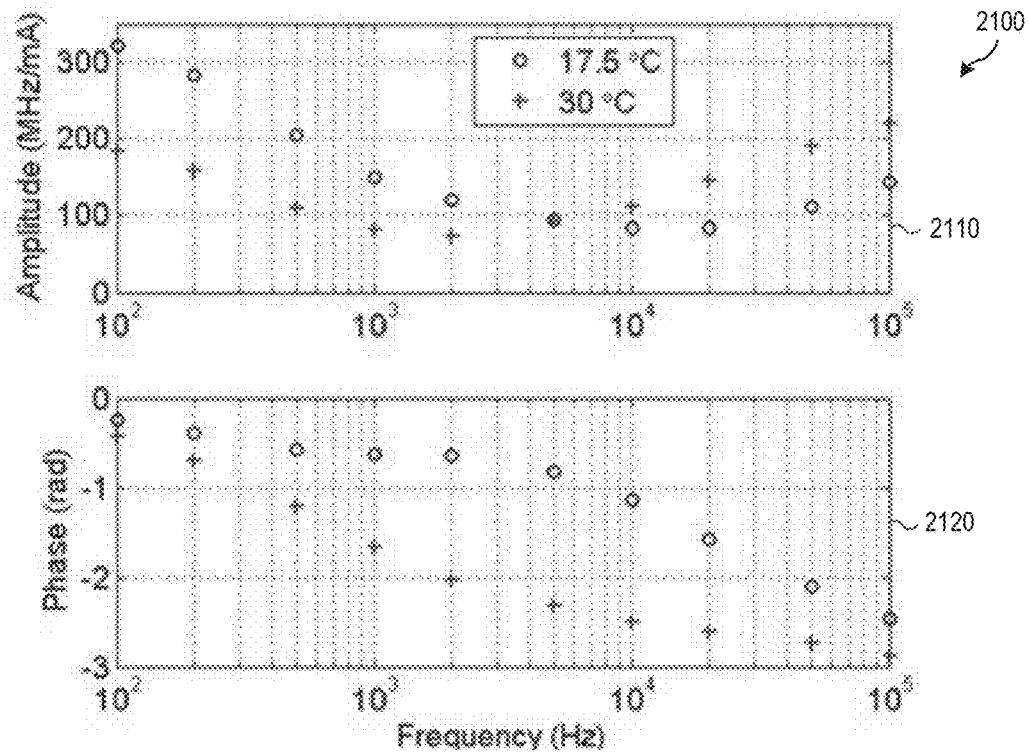
FIG. 21 is a graph of a frequency modulation response function for a 2004 nm laser diode operated at two different temperatures, according to a disclosed embodiment.

For laser diodes that are commonly used for WMS measurements there are several parameters that can be adjusted to configure a desired value of the phase shift between AM and WM including: the DC bias current, the diode temperature and the WM frequency. FIG. 21 shows the WM response function for a 2004 nm distributed-feedback laser diode used for $CO_2$ WMS measurements, and illustrates how the changes in the laser temperature and WM modulation frequency can be tuned to achieve a $\pi/2$ phase shift between AM and WM modulations. In this case tuning the diode temperature to 17.5° C. and setting the modulation frequency at 20 kHz results in a π/2 phase shift between AM and WM modulations, and thereby enables the SNR benefits shown in FIG. 20.

FIG. 21 is a graph 2100 of a frequency modulation response function for a 2004 nm laser diode operated at two different temperatures. A π/2 phase shift between AM and WM components is achieved at an operating temperature of 17.5° C., a bias current of 100 mA, and a 20 kHz modulation frequency. FIG. 21 shows the amplitude response by frequency 2110 and the phase response by frequency 2120.

Figure 22:
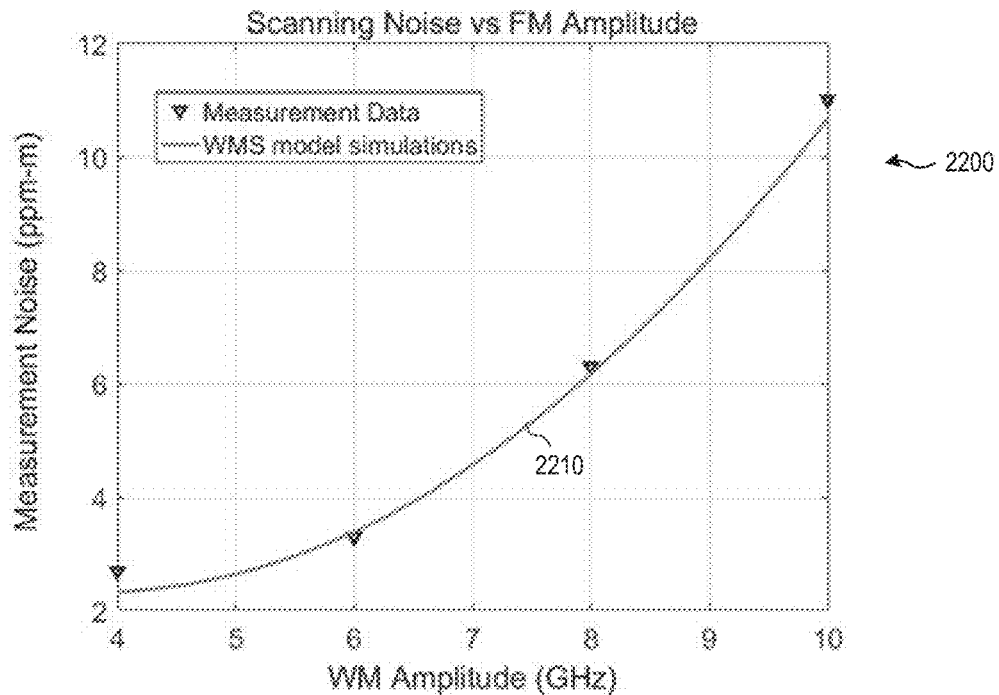
FIG. 22 is a graph showing the noise on spatially-scanned path-integrated concentration measurements of methane at 1645 nm versus wavelength modulation amplitude (expressed in optical frequency units) for a diffuse target with 0.5 mm of surface roughness, according to a disclosed embodiment.

Another modulation parameter that can be configured to reduce the noise on spatially-scanned WMS measurements is the WM amplitude. FIG. 22 shows spatially-scanned WMS measurements of atmospheric methane (P=850 mbar and T=295 K) using the 1645 nm absorption line from a diffuse target with 0.5 mm surface roughness.

FIG. 22 is a graph 2200 showing the noise on spatially-scanned path-integrated concentration measurements of methane at 1645 nm versus wavelength modulation amplitude (expressed in optical frequency units) for a diffuse target with 0.5 mm of surface roughness. The noise standard deviation increases with increasing wavelength modulation amplitude.

The measured values are plotted against a theory curve 2210 computed using a numerical model of the WMS measurement. The measurement values and theory curve represent the measured and expected one-standard deviation integrated-path concentration noise. For this level of surface roughness the measurements and theory show that using a WM amplitude near 4 GHz leads to minimized measurement noise.

In contrast, a WM amplitude of 6 GHz is required to minimize measurement noise for stationary WMS measurements. For the spatially-scanned case, further reducing the WM amplitude below 4 GHz does not lead to further noise reduction. This is due to the fact that the sensitivity of the WMS measurement reduces rapidly for lower WM amplitudes, approaching zero sensitivity at a zero WM amplitude. The noise behavior for spatially-scanned WMS measurements shown in FIG. 22 represents just one special case of a more complicated noise behavior for scanned WMS measurements from diffuse targets.

In general, speckle interference caused by the surface roughness and macroscopic structure of diffuse targets may behave similarly to the interference from collections of spatially-unresolved, low-quality-factor etalons. The received wave fronts from the collection of etalons contained in each diffraction-limited spot within the WMS receiver image interfere to form the speckle modulation in that speckle cell. The speckle modulations contained in all speckle cells imaged by the WMS receiver are then averaged by the photodetector to form the speckle noise on the WMS signal.

Figure 23:
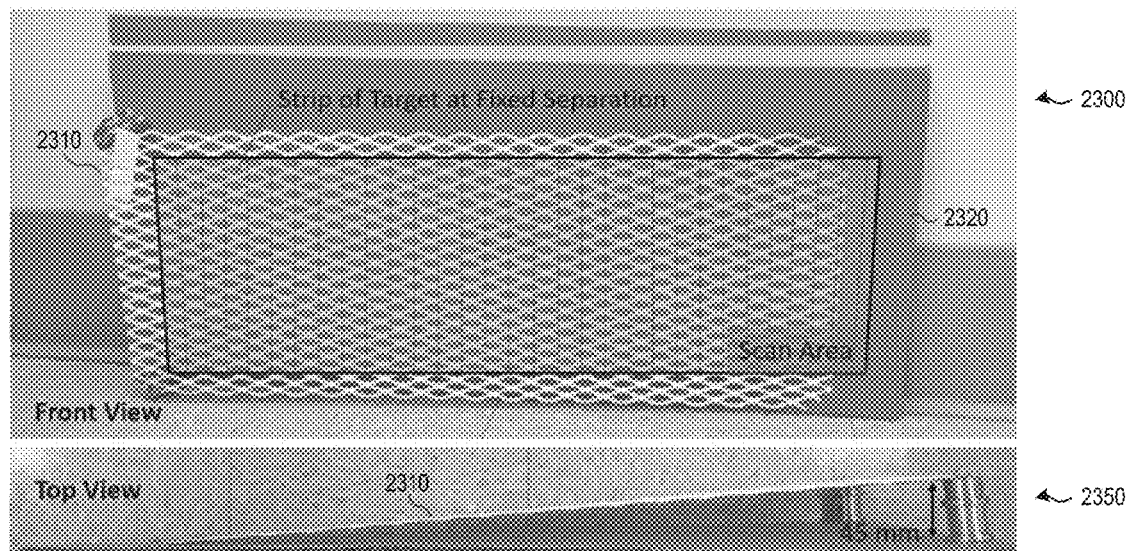
FIG. 23 shows views of a topographic target for measurements of speckle noise versus the separation between two surfaces on spatially-scanned WMS measurements, according to a disclosed embodiment.

To better illustrate the analogy between structured diffuse targets and collections of etalons, consider the target shown in FIG. 23.

FIG. 23 shows views 2300, 2350 of a topographic target for measurements of speckle noise versus the separation between two surfaces 2310, 2320 on spatially-scanned WMS measurements. The front view 2300 shows the scan area and strips of the target with fixed separation between front surface 2310 and the back surface 2320, while the top view 2350 shows the surface separation versus lateral position.

This target has two diffuse surfaces 2310, 2320 that are separated in range. The first surface 2310 is a grate that scatters some of the WMS beam and allows some to pass to the second surface 2320. The range separation between the surfaces 2310, 2320 varies between 0 mm and 45 mm across the target. The gas concentration speckle noise can be measured versus target separation by analyzing narrow vertical strips of a gas concentration image.

Figure 24:
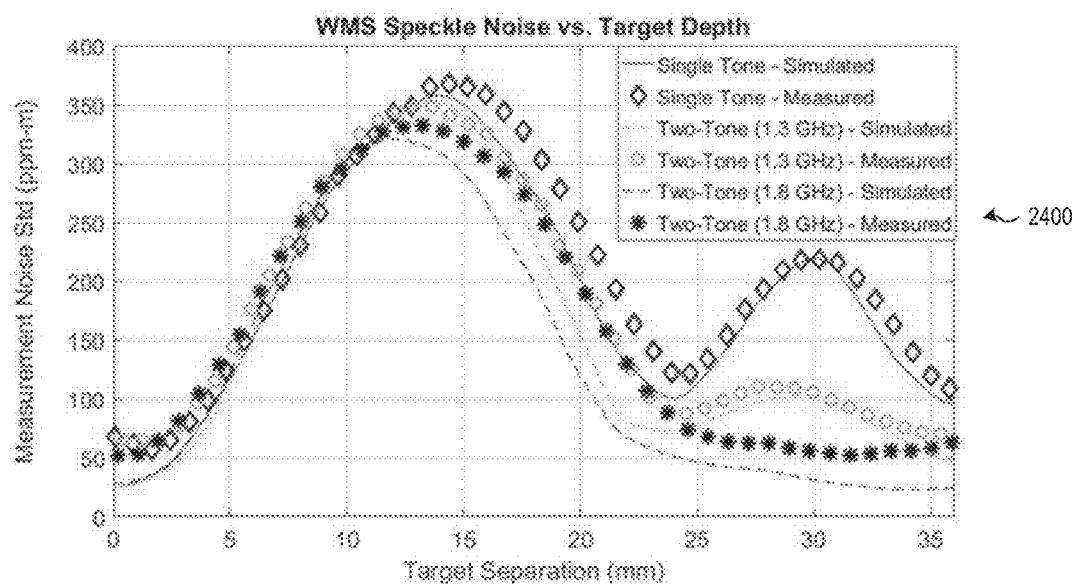
FIG. 24 is graph of noise comparison for single-tone and two-tone WMS measurements and measurement simulations of atmospheric $CO_2$ using the topographic target shown in FIG. 23, according to a disclosed embodiment.

FIG. 24 is graph 2400 of noise comparison for single-tone and two-tone WMS measurements and measurement simulations of atmospheric $CO_2$ using the topographic target shown in FIG. 23. The single-tone WMS measurements and simulations were configured with a modulation frequency of 40 kHz and a WM amplitude of 5.2 GHz. The two-tone WMS measurements and simulations were configured with a modulation frequency of 40 kHz and a WM amplitude of 5.2 GHz for the first tone, and a modulation frequency of 4 kHz and WM amplitudes of 1.3 GHz and 1.8 GHz for the second tone. The two-tone WMS configurations show improved noise performance compared to single-tone WMS configuration for surface separations above 14 mm, which corresponds to 1 free spectral range of the optical bandwidth of the $1^{st}$ WMS tone.

FIG. 24 is a graph 2400 that shows data from atmospheric $CO_2$ measurements using the target shown in FIG. 23 for three different WMS modulation configurations. These measurements were performed on the 2004 nm $CO_2$ absorption line with a measurement duration of 0.5 ms. The first configuration, labeled single tone, had a WM amplitude of 5.2 GHz and a modulation frequency of 40 kHz. Clear fringes are present in the single tone gas concentration noise. The fringes can be understood by considering the phase shift between the waves scattered by the first and second surfaces as a function of the optical bandwidth of the WMS modulation waveform. The spatial separation required for a 2π phase shift between reflections from the first and second surface is given by, $$\Delta r = \frac{c}{2B} = \frac{3e8 \text{ m/s}}{2 \times 10.4 \text{ GHz}} = 14.4 \text{ mm}, \quad (19)$$

where B is the optical bandwidth of the WMS modulation waveform, and is equal to twice the WM amplitude. Peaks are observed in the single-tone noise at separations of 14.5 mm and 29.5 mm, corresponding to integer multiples of the spatial length required for a 2π phase shift between reflections from the first and second target surfaces. The fringed structure of the single tone data indicates that the noise peaking should appear at longer surface separations for is the underlying reason why smaller WM amplitudes lead to lower gas concentration noise for the low surface roughness measurements and simulations shown in FIG. 22.

The two-tone WMS modulation configurations used the same first-tone amplitude and frequency (5.2 GHz and 40 kHz) as the single-tone case, and also include a second wavelength modulation at frequency 4 kHz with amplitudes 1.3 GHz and 1.8 GHz. The 4 kHz modulation frequency was chosen to allow for two complete cycles of the second modulation tone within each 0.5 ms measurement duration. FIG. 24 shows reduced gas concentration noise for the two-tone configurations for target separations exceeding 14 mm. The noise reduction is due to increased speckle cell averaging for larger surface separations that is facilitated by the second modulation tone. Noise suppression for targets with large range extent within the WMS beam can also be achieved through a chirping the first WMS tone, or through a combination of a chirped first WMS tone with a second WMS tone.

It is important to note that this implementation of two-tone WMS spectroscopy is conceptually different from examples of two-tone frequency modulation (FM) spectroscopy or frequency-swept WMS that can be found in the literature. Previously demonstrated two-tone (FM) spectroscopy is implemented with high frequency, spectrally-resolved sidebands at frequencies of hundreds of MHz to several GHz using optical modulators. The second FM tone is typically applied to enable detection of the FM spectroscopy signal at much lower detection frequencies. This allows the use of higher sensitivity detectors for low light spectroscopic applications. The implementations of frequency swept WMS measurements are typically performed for the purpose of determining the frequency response function of a laser and for calibrating WMS measurements. In contrast, the present embodiment uses multiple-tone WMS measurements for the purposes of reducing measurement noise from diffuse targets.

The data in FIG. 24 is plotted against computer simulations of the three WMS measurement configurations using an electric-field-based version of WMS model outlined in Equations 14-17. This model also includes the transmitter and receiver properties and as well as the target properties to enable modeling of the expected speckle interference. A simplified representation of the two-surface target was inputted into these simulations as a square grid structure for the first surface and randomly distributed roughness for both surfaces with root-mean-squared amplitude of 0.2 mm. Good agreement was observed between the simulations and measurements for both the magnitudes of the gas concentration noise and the variations of the noise versus surface separation. The broadened peaks in the data compared to the simulations may be due to non-uniformity of the separation between the first and second target surfaces across the vertical extent of the measurement strips shown in FIG. 23.

The simulation model enables exploration of the expected measurement noise for a variety of target types and measurements scenes, and allows for the design of modulation waveforms that are tailored to provide minimized gas concentration noise for a particular measurement scene. This capability opens the door for more advanced implementations of gas imaging where 3D spatial data and noise on gas concentration measurements can be used to determine the optimal WMS modulation configuration to use for a particular measurement scene. The ability to design optimal WMS modulation waveforms based on the type of target or measurement scene may one day lead to recipes for lists of preprogrammed WMS modulation waveforms that can be changed on demand during a measurement mission to minimize the gas concentration noise for the various targets within the measurement scene.

CONCLUSION

This disclosure is intended to explain how to fashion and use various embodiments in accordance with the invention rather than to limit the true, intended, and fair scope and spirit thereof. The foregoing description is not intended to be exhaustive or to limit the invention to the precise form disclosed. Modifications or variations are possible in light of the above teachings. The embodiment(s) was chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled. The various circuits described above can be implemented in discrete circuits or integrated circuits, as desired by implementation.

What is claimed is:

1. A method comprising:
    modulating an output wavelength of a laser such that a modulation amplitude, modulation frequency, and modulation phase of the laser output are known;
    transmitting a portion of the laser output to a surface;
    receiving a portion of the laser output scattered from the surface;
    producing a laser wavelength modulation spectroscopy signal from the received scattered laser output;
    using output laser parameters to create an approximate functional form or a look-up table of an absorption sensitivity coefficient ($\gamma$); and
    computing a gas concentration using the laser wavelength modulation spectroscopy signal with the approximate functional form or the look-up table of the absorption sensitivity coefficient ($\gamma$).

2. The method of claim 1, wherein
    the absorption sensitivity coefficient ($\gamma$) is determined also as a function of temperature, pressure, and/or absorption strength.

3. A method comprising:
    modulating an output of a laser;
    for a gas concentration measurement, determining that a relative phase between an output amplitude modulation and an output wavelength modulation of the modulated laser output is to be a $\pi/2$ relative phase;
    selecting a laser and/or laser operational parameters with a $\pi/2$ relative phase between the output amplitude modulation and the output wavelength modulation of the modulated laser output based on the determined $\pi/2$ relative phase;
    for the gas concentration measurement, using the modulated laser output with the selected $\pi/2$ relative phase to perform laser wavelength modulation spectroscopy, whereby use of the $\pi/2$ relative phase reduces noise on a wavelength modulation spectroscopy signal that is due to speckle interference.

4. The method of claim 3, wherein
    the determining the relative phase is accomplished by empirical measurements or by inferring from known behavior of similar lasers.

5. The method of claim 3, wherein
    the laser operational parameters include a laser bias current, a laser temperature, an input modulation amplitude, or an input modulation frequency.

6. A method comprising:
    modulating an output of a laser at a plurality of different modulation frequencies, wherein at least two of the modulation frequencies are less than a gas absorption linewidth;
    transmitting a portion of the laser output to a surface;
    spatially scanning the transmitted portion of the laser output;
    using the modulated laser output to perform laser wavelength modulation spectroscopy to determine a gas absorption
    whereby the use of the plurality of modulation frequencies reduces noise on the wavelength modulation spectroscopy signal that is due to speckle interference.

7. The method of claim 6, wherein
at least one of the plurality of modulation frequencies is selected for an integer multiple of a cycle within the measurement duration.

8. The method of claim 6, wherein
the output of the laser is modulated in both wavelength and amplitude for each of at least two of the plurality of modulation frequencies.

9. A method comprising:
modulating an output wavelength of a laser;
transmitting a portion of the laser output to a surface;
spatially scanning the transmitted portion of the laser output;
receiving a portion of the laser output scattered from the surface;
producing a laser wavelength modulation spectroscopy signal from the received scattered laser output; and
filtering the laser wavelength modulation spectroscopy signal to reduce measurement noise caused by spatially scanning the transmitted portion of the laser output.

10. The method of claim 9, wherein
filtering the laser wavelength modulation spectroscopy signal comprises applying an nth-order polynomial fit to reduce low-frequency biases from the wavelength modulation spectroscopy signal.

11. The method of claim 9, wherein
filtering the laser wavelength modulation spectroscopy signal comprises applying a window function to the wavelength modulation spectroscopy signal.

12. The method of claim 9, wherein
filtering the laser wavelength modulation spectroscopy signal comprises applying a window function or nth-order polynomial filtering to overlapping portions of a measurement signal such that a measurement duty cycle is substantially greater than 50%.

* * * * *